(12) United States Patent
Allen et al.

(10) Patent No.: US 6,383,538 B1
(45) Date of Patent: May 7, 2002

(54) PRODUCING MEAT WITH ENHANCED SHELF-LIFE

(75) Inventors: Vivien Gore Allen, Lubbock; Kevin R. Pond, Wolfforth, both of TX (US)

(73) Assignee: Texas Tech University, Lubbock, TX (US)

(*) Notice: Subject to any disclaimer, the term of this patent is extended or adjusted under 35 U.S.C. 154(b) by 0 days.

(21) Appl. No.: 09/333,658

(22) Filed: Jun. 16, 1999

Related U.S. Application Data

(63) Continuation-in-part of application No. 09/032,104, filed on Feb. 27, 1998.

(51) Int. Cl.[7] .......................... A21D 10/02; A23L 1/31; A23K 1/17; A61K 35/78

(52) U.S. Cl. ................ 426/129; 426/574; 424/442; 424/195.1; 514/783

(58) Field of Search ............................... 426/129, 574; 514/783; 424/442, 195.1

(56) References Cited

U.S. PATENT DOCUMENTS 5,843,762 A  12/1998  Moll ........................ 435/257.1

OTHER PUBLICATIONS

Correale, K. K., et al., Meat Science 18, 161–172 (1986).
Schmidt, R. E., et al., Proc. 1997 Amer. Forage and Grassl. Counc., Georgetown, TX, 6:158–162.
Coelho, R. W. et al., Proc. 1997 Amer. Forage and Grassl. Counc., Georgetown, TX, 6:163–167.
Allen, V. G., et al., Proc. 1997 Amer. Forage and Grassl. Counc. Counc., Georgetown, TX, 6:168–172.
Saker, K. E., et al., Proc. 1997 Amer. Forage and Grassl. Counc., Georgetown, TX, 6:178–182.
Fike, J. H., et al., Proc. 1997 Amer. Forage and Grassl. Counc., Georgetown, TX, 6:153–157.
Kim, C. S. et al., The Effect of Dietary Sargassum–Natans and Ascophyllum–Nodosum on *Salonella Gallinarum* Infection in Chicks, BIOSIS (AN 1969:8848).
Herskoviz, R., et al., Differential effects of Polysulfated polysaccharide on experimental encephalomyelitis, proliferation of autoimmune T cells, and inhibition of heparanase activity, BIOSIS (AN 1996:22174).
Matsuzaki, S., et al., Application of seaweeds to human nutrition and medicine CA (AN97:4974).
Nishizawa, K., Seaweed as food for controlling diseases in elderly patients, CAPLUS (AN 1998:590009).
Kim, C. S. The Effects of Dietary Sargassum–Natans and Ascophyllum–Nodosum on *Salonella–Gallinarum* Infection in Chicks, BIOSYS (An 1973:82740).
Charreau, B., et al., Efficiency of fucans in protecting procine endothelial cells against complement activation and lysis by human serum, BIOSIS (AN 1997:190627).
Blondin, C., et al., Relationships between chemical characteristics and anticomplementary activity of fucans, BIOSYS (AN 1996:188236).
Ren, D., et al., Study on Antihypertensive and Antihyperlipidemic Effects of Marine Algae, BIOSIS (An 1994:487915).

(List continued on next page.)

*Primary Examiner*—Russell Travers
*Assistant Examiner*—Shengjun Wang

(57) ABSTRACT

A method of obtaining beef of increased shelf-life comprises the step of grazing cattle on forage on or into which seaweed supplement has been incorporated or directly feeding seaweed supplement to cattle during the feedlot finishing period. A method of obtaining pork of increased shelf-life comprises the step of feeding seaweed supplement to pigs during the nursery period of their life cycle. A preferred seaweed is *Ascophyllum nodosum*.

36 Claims, 13 Drawing Sheets-

OTHER PUBLICATIONS

Klinger, M. M., et al., Anti–HIV Activity of Sulfated Polysaccarides from the Brown Seaweed *Ascophyllum nodosum*, DRUGU M (AN 91–25081).

Blunden, G., et al., Medicinal and Pharmaceutical Uses of Algae, DRUG U TMPS (AN 87–01915).

Brochure titled Field Trial Summaries, Inpact of Acadian Seaplants Seaweed Extract on Aricultural Crops Acadian Seaplants Limited, Nova Scotia, Canada (undated).

Product and Technical Information, *Ascophylluns nodosum* Kelp Meal and Flour, Acadian Seaplants Limited, Nova Scotia, Canada (Jan. 10, 1998).

Information Sheet on Acadian Seaplants Seaweed Extract, Acadian Seaplants Limited, Nova Scotia, Canada, Jan. 8, 1998.

Brochure titled Acadian Seaplants Seaweed Extract Soluble Powder or Liquid, Acadian Seaplants Limited, Nova Scotia, Canada, (undated).

Information Sheet titled Product and Technical Information, General Home and Garden Use, Acadian Seaplants Limited, Nova Scotia, Canada (Sep. 5, 1998).

Brochure titled Acadian on Grapes, Grower's Success Series, Acadian Seaplants Limited, Nova Scotia, Canada (undated).

Brochure titled Acadian Seaplants Kelp Meal (100% *Ascophyllum nososum*) For Soil Applications, Acadian Seaplants Limited, Nova Scotia, Canada (undated).

CA Abstract, AN 1998:73377, Wakebe, 1998.*

Derwent Abstract, Derwent AN 1980–29751, Donnelly et al., 1980.*

Hobbs, D., The New Farm May/Jun. 1994, 26–28.

Klober, K., Small Farm Today, 8/96, p. 10.

Hobbs, D., "The Quest for a Water Soluble Mineral" (undated).

Hobbs, D., "Kelp Cures Copper" (undated).

Morrison, F. B., Fields and Feeding, The Morrison Publishing Company, Ithaca, NY (1957), p. 554.

Dennis, S.B., et al., J. Anim. Sci. 76, 2687–2693 (1998).

Fike, J. H., Masters Thesis titled Influence of Seaweed Extract and Other Plant Growth Regulators on Growth, Persistence and Quality of Tall Fescue and Their Potential to Alleviate Tall Fescue Toxicity to Livestock (1995).

Hobbs, D., "Soil Amending Attributes of Kelp Meal" (undated).

Hobbs, D., "Benefit of Foliar Applied Seaweed Extract" (undated).

Sen, T. L. Seaweed and Plant Growth (1987), pp 7–4, 7–5.

Buttery, S., Influence of Acremonium Coenophialum on Fescue Arundinacea Growth, Chemical Composition, Digestability and Tall Fescue Toxicities; Ph.D. dissertation, 1989, abstract and pp 36, 84 and 86.

Okai, Y., et al., J. Sci. Food Agric. 72, 455–460 (1966).

Okai, Y., et al., J. Sci. Food Agric. 76, 56–62 (1998).

Woodward, L., Vistas, Texas tech Research, Fall 1999, vol. 8, No. 1, pp 20–25.

Saker, K. E., et al., J. Anim. Sci. 76, 2694–2700 (1998).

* cited by examiner

PRODUCING MEAT WITH ENHANCED SHELF-LIFE

CROSS-REFERENCE TO RELATED APPLICATIONS

This is a Continuation-In-Part of patent application Ser. No. 09/032,104 filed Feb. 27, 1998.

TECHNICAL FIELD

This invention relates to a method of producing meat of increased shelf-life.

BACKGROUND OF THE INVENTION

Background in respect to beef and pork production is set forth below.

We turn firstly to beef production. Beef is typically obtained from cattle (beef cattle or dairy cattle) that have grazed in pastures and have fed in feedlots. About two years after birth, the animals are slaughtered and primal cuts are obtained. The primal cuts are usually vacuum packaged to preserve freshness, and the vacuum packaged primal cuts are sent to supermarkets or other meat distribution businesses where the vacuum packaging is removed and the primal cuts are cut into smaller cuts which are repackaged or displayed in a case for sale. As time passes beyond the period of optimum sale, the pieces of beef lose their desirable bright cherry red color and darken due to browning or otherwise discolor and become non-uniform in color (two-toning) and must be sold at lower than premium prices, and eventually are converted to hamburger and sold at much lower prices. Extending the shelf-life of beef by preserving optimum color is a sought after goal whereby the stores selling the beef can obtain higher return on beef that they purchase.

We turn now to pork production. The typical life cycle for swine for pork production consists of remaining with the mother for 14 to 28 days, and being weaned and being placed in a nursery for three to five weeks, being moved to a finishing barn where they are kept until reaching 220 to 275 pounds (three to four months), and finally transportation for slaughter. The shelf-life of meat after slaughtering is about 6 days. Toward the end of the 6-day period, the red color of the meat becomes less bright causing reduced appeal for sale.

SUMMARY OF THE INVENTION

One object herein is to provide beef of increased shelf-life whereby it remains salable at optimum prices on the grocery store shelf for at least one day longer than beef not obtained by the methods herein.

In one embodiment herein, this object is obtained by a method comprising the steps of: (a) grazing cattle on forage (in pastures) on or into which seaweed supplement has been incorporated, and (b) slaughtering the cattle to obtain primal cuts of beef; thereby to obtain beef which is salable at higher prices for a longer period of time than if seaweed supplement was not incorporated (i.e., the first method herein). Forage on or into which seaweed supplement has been incorporated is sometimes referred to hereinafter as seaweed treated.

In a second embodiment herein, this object is obtained by a method comprising the steps of: (a) directly feeding seaweed supplement to cattle during the feedlot finishing phase (period) of the life cycle for beef production; and (b) slaughtering the cattle to obtain primal cuts of beef, thereby to obtain beef which is salable at higher prices for a longer period of time than if seaweed supplement was not fed (i.e., the second method herein).

Another object herein is to provide pork of brighter red color.

This object is obtained by a method comprising the steps of (a) feeding seaweed supplement to swine, for example, during the nursery phase (period) of the life cycle of swine raised for meat production; and (b) slaughtering the swine to obtain pork which is of brighter red color than if seaweed supplement was not fed (i.e., the third method herein). When the seaweed supplement is seaweed extract, data indicates longer shelf-life for sale at optimum prices is obtained.

DETAILED DESCRIPTION

Figure 1:
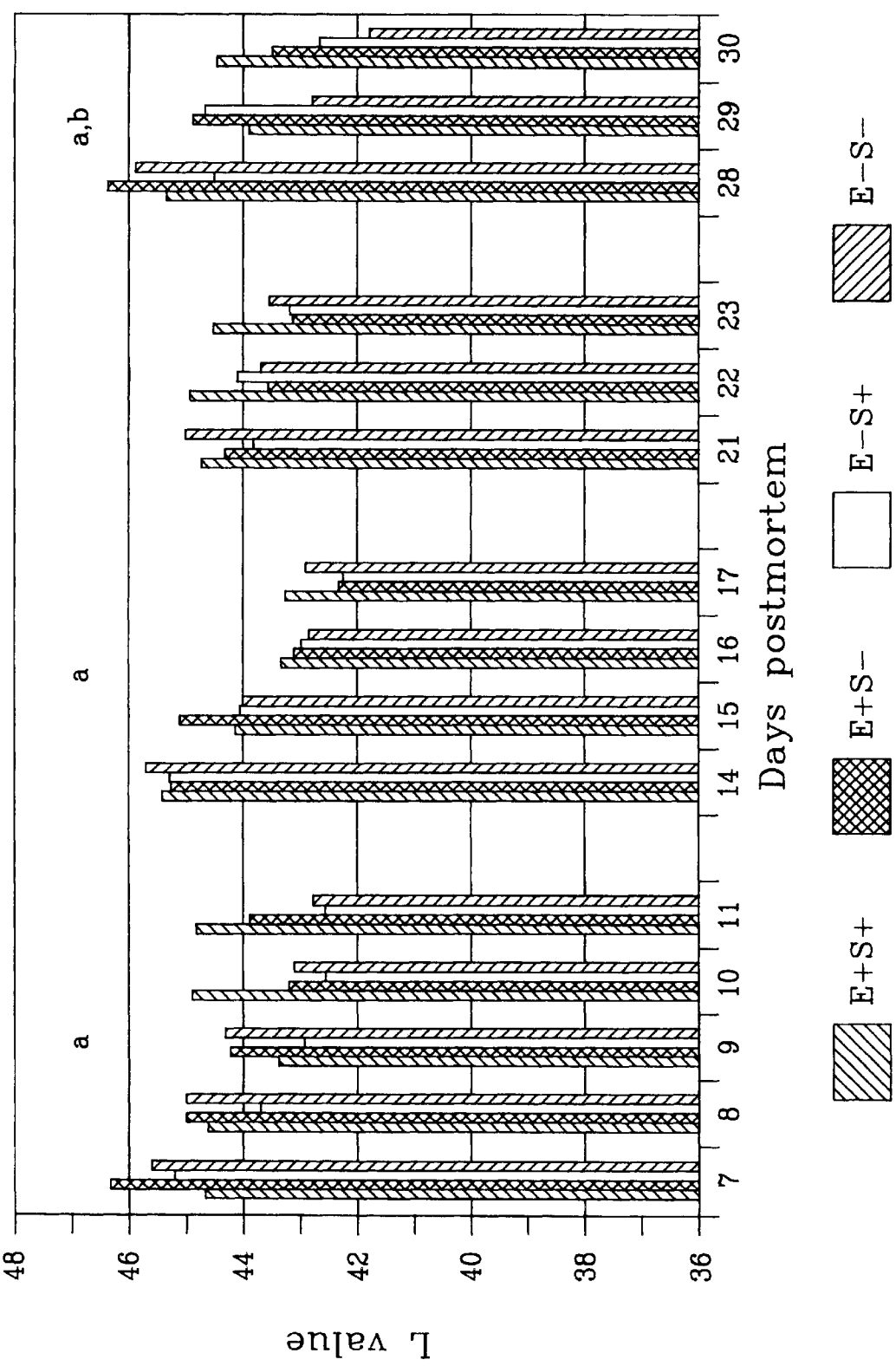
FIG. 1 depicts bar graphs showing CIE Hunter $L^*$ values in beef on removal from vacuum packaging on day 7, 14, 21 and 28 post mortem on steers that had grazed endophyte-infected (E+) and non-infected (E−) tall fescue that was either treated (S+) or untreated (S−) with seaweed extract as described in Example I.

We turn now to the first method herein.

The cattle can be beef cattle or dairy cattle that are not used for milk production or breeding purposes.

The forage in the pasture can be any forage suitable for grazing of cattle. One important forage is tall fescue (*Festuca arundinacea Schreb*) which is grown on over 14 million hectares of land in the United States. Other forages include, for example, orchard grass (*Dactylis glomerata L.*), bluegrass (*Poa pratenisis L.*), bermudagrass (*Cynodon dactylon L.*), and ryegrass (Lolium spp.).

The first method herein is applicable to and is especially advantageous when the forage is endophyte fungus infected. The fungus helps the plant tolerate stresses such as drought and insects. Endophyte fungus which infects tall fescue is *Neotyphodium coenophialum*. Endophyte fungus which infects ryegrass is *Acremonium lolii*.

The seaweed from which the seaweed supplement is obtained can be from any of the various seaweed plant classifications, preferably those that have been utilized in agriculture and include seaweeds from the plant orders Laminariaceae, Fucaceae and Gigartinaceae. Genus groups include Ascophyllum, Laminaria, Durvillea, Macrocystis, Chondrus and Ecklonia. The seaweed for the preferred seaweed supplement herein is from the genus Ascophyllum which belongs to the order Fucaceae and is *Ascophyllum nodosum*. *Ascophyllum nodosum* is a brown seaweed which grows along the North Atlantic shorelines of Canada, the United States, and Europe.

The seaweed supplement can be, for example, seaweed extract or seaweed meal.

We turn now to seaweed supplement which is seaweed extract.

Seaweed extract is water soluble and can be obtained by alkaline hydrolysis extraction. A preferred seaweed extract is obtained by alkaline hydrolysis extraction from *Ascophyllum nodosum*; a commercial product of this kind is available from Acadian Seaplants Limited of Nova Scotia Canada, and is sold under the tradenames Acadian Soluble Seaweed Extract Powder (powder form) and Acadian Liquid Seaweed Concentrate (liquid form). Acadian Soluble Seaweed Extract Powder is made up of brownish-black crystals, has a seaweed-like odor, is 100% soluble in water and has a pH of 10–10.5 in water and typical analysis shows by weight 6.5% maximum moisture, 45–55% organic matter, 45–55% ash (minerals), 1.0–2.0% total nitrogen (N), 2.0–4.0% available phosphoric acid ($P_2O_5$), 18.0–22.0% soluble potash ($K_2O$), 1.0–2.0% sulfur (S), 0.2–0.5% magnesium, 0.1–0.2% calcium, 3.0–5.0% sodium, 75–150 ppm boron, 75–250 ppm iron, 8–12 ppm manganese, 1–10 ppm copper, 25–75 ppm zinc; alginic acid, mannitol, and laminarin carbohydrates; cytokinin, auxin and gibberellin growth promoters; and the following average grams of amino acid per 100 grams of protein: alanine, 3.81; arginine, 0.22; aspartic acid, 5.44; cystine, trace; glutamic acid, 7.69; glycine, 3.16; histidine, 0.42; isoleucine, 1.94; levcine, 4.84; lysine, 1.33; methonine, 1.39; phenylalanine, 2.82; proline, 4.42; serine, 0.14; threonine, 1.27; tyrosine, 1.80, and valine, 3.46.

Seaweed extract is preferably applied to pasture forage as a water solution at the beginning of the grazing season and in the middle of the grazing season. The seaweed extract can be applied, for example, in an amount ranging from 0.3 kg/ha to 5 kg/ha, e.g., 1 to 4 kg/ha, and an application amount of 3.4 kg/ha (3 lbs/acre) has been used with good advantage. The seaweed extract (powder form) is readily dissolved in 20 to 40 gallons of water per acre. Application is preferably carried out by spraying the water solution on the pasture forage using a commercial field-type of sprayer.

We turn now to seaweed supplement which is seaweed meal or flour.

The seaweed meal or flour can be obtained by dehydrating the seaweed, for example, by solar drying followed by low heat finish drying and processing the dehydrated material into a granular meal or four. A preferred seaweed meal is obtained from *Ascophyllum nodosum* and is available from Acadian Seaplants Limited of Nova Scotia, Canada, and is sold under the tradename Acadian Kelp Meal. A typical analysis of Acadian Kelp Meal shows the following approximate weight percentages: moisture 12.0%, crude protein 6.0%, crude fiber 6.0%, ash (minerals) 22.0%, fat 20%, and carbohydrates 52.%. Analysis of Acadian Kelp Meal for carbohydrates gives by weight 18.0–27.0% alginic acid, 3.8–8.0% mannitol, 2.0–5.0% laminarin, and 20.0–22.0% other sugars. Analysis of Acadian Kelp Meal for minerals gives 50–150 ppm aluminum, 5–15 ppm barium, <1 ppm beryllium, 80–100 ppm boron, <1 ppm cadmium, 1.0–3.0% calcium, 1.0–3.0% chloride, 1–2 ppm chromium, <1 ppm cobalt, 1–10 ppm copper, <1,000 ppm iodine, 100–500 ppm iron, <1 ppm lead, 0.5–1.0% magnesium, 10–50 ppm manganese, <1 ppm mercury, <2 ppm molybdenum, <1 ppm nickel, 0.5–2.0% nitrogen, 0.1–0.2% phosphorus, 1.5–2.5% potassium, 3–4 ppm selenium, 2.4–4.0% sodium, 100–600 ppm strontium, 2.0–3.0% sulfur, <10 ppm tin, 1–10 ppm titanium, 2–6 ppm vanadium and 10–50 ppm zinc. Analysis of Acadian Kelp Meal for vitamins gives 0.1–0.4 ppm biotin, 30–60 ppm carotene, 0.1–0.5 ppm folic acid, 0.1–0.5 ppm folinic acid, 10–30 ppm niacin, 5–10 ppm riboflavin, 1–5 ppm thiamin, 150–300 ppm tocopherols, 100–2,000 ppm vitamin C, <0.004 ppm vitamin $B_{12}$, and <10 ppm vitamin K. Analysis of the amino acid content for Acadian Kelp Meal gave the following expressed as grams of amino acid per 100 g of protein nitrogen: alanine 5.3, arginine 8.0, aspartic acid 6.9, cystine (trace), glycine 5.0, glutamic acid 10.0, histidine 1.3, isoleucine 2.8, leucine 4.6, lysine 4.9, methionine 0.7, phenylalanine 2.3, proline 2.6, serine 3.0, threonine 2.8, tryptophan (trace), tyrosine 0.9, and valine 3.7.

Seaweed meal is preferably applied to a pasture to provide seaweed treated forage by application in dry form and solubles from seaweed meal dissolve after application so that the solubilized material is available for foliar uptake and/or leaches into the ground and is taken up by the forage. The seaweed meal can be applied, for example, in an amount of 0.3 to 10 kg per acre.

The cattle preferably are grazed on the seaweed extract treated pasture forage for 100 to 210 days (e.g., 180 to 200 days) in the spring and summer seasons in the year after birth and then are preferably feedlot finished over a period ranging from 75 to 200 days, e.g., 130 to 160 days. For feedlot finishing, the cattle in Example I hereinafter were fed a diet based on steamflaked milo (*Sorghum bicolor*) and cottonseed hulls (*Gossipium hirsutum*) that is typical of feedlot finishing diets; however, the diet for feedlot finishing may be based on other ingredients including corn (*Zea mays*), wheat (*Triticum aestivum*), barley (*Hordeum vulgare*) or other grains and is most typically based on corn.

After slaughtering, e.g., within 36 to 48 hours after slaughtering, the primal cuts obtained are preferably vacuum packaged. The primal cuts are sent to grocery stores and meat markets within five to ten days, where they are normally cut into smaller cuts and displayed in plastic film covered packages or in display containers.

The number of days after removal from vacuum packaging that the meat is salable at optimum prices on the grocery store shelf depends on the number of days the primal cuts are retained in the vacuum packaging. If the primal cuts are cut into smaller pieces and displayed for sale immediately after slaughter, without the treatment herein shelf life at optimum prices can be five to ten days and can be up to two weeks but usually is less than seven days. If the primal cuts are removed from vacuum packaging on day 7 after slaughter, without the treatment herein darkening of red color, discoloration (formation of green cast), and non-uniform color (two-toning) to an unacceptable degree can occur on day 4 after removal from vacuum packaging. If the primal cuts are removed from vacuum packaging on day 14 after slaughter, without the treatment herein, discoloration and non uniform color can occur on day 3 after removal from vacuum packaging. If the primal cuts are removed from vacuum packaging on day 21 after slaughter, without the treatment herein darkening of red color, discoloration, unacceptable browning and lack of uniformity can occur on day 2 after removal from vacuum packaging. If the primal cuts are removed from vacuum packaging on day 28 after slaughter, without the treatment herein discoloration and non-uniformity can occur on day 2 after removal from vacuum packaging.

Advantages are obtained with the first method herein both when the forage is endophyte infected and when the forage is not endophyte infected. With tall fescue, endophyte infected or not endophyte infected, with treatment herein, when primal cuts are removed from vacuum packaging seven days after slaughter, meat from the primal cuts have been found to remain of quality sufficient to be sold at optimum prices and is desirable for sale on the fourth day after removal from vacuum packaging. With tall fescue, endophyte infected and not endophyte infected, with the treatment herein, when the primal cuts are removed from vacuum packaging 28 days after slaughter, meat from the primal cuts has been found to remain of quality sufficient for sale at optimum prices and is desirable for sale on the second day after removal from vacuum packaging. With tall fescue grass which is endophyte infected, with the treatment herein, when primal cuts are removed from vacuum packaging 21 days after slaughter, meat from the primal cuts has been found to remain of sufficient quality for sale at optimum prices and is desirable for sale on the second day after removal from vacuum packaging. With tall fescue grass which is not endophyte infected, with the treatment herein, when primal cuts are removed from vacuum packaging 14 days after slaughter, meat from the primal cuts has been found to remain of sufficient quality for sale at optimum prices and is desirable for sale on the third day after removal from vacuum packaging.

The findings herein show that shelf life was improved by the treatment herein to the extent of color, discoloration, uniformity and browning properties being such that the meat remained salable at optimum prices (prices charged for meat with little or no color deterioration) on the grocery store shelf at least one day longer than meat from steers grazed on non-seaweed treated pastures. Presence of endophyte in tall fescue when pastures were treated with seaweed had the greatest beneficial effect on lengthening shelf life of meat but this effect of seaweed on improving shelf life was also observed in meat from cattle grazing on pastures with tall fescue that was not endophyte infected.

In one alternative, the beef is maintained on store shelves at optimum prices for a period (e.g., one day) longer than is the case without the treatment of the first method herein.

We turn now to the second method herein where seaweed supplement is directly fed to cattle during the feedlot finishing phase of the life cycle for beef production.

In a typical life cycle for beef production, calves remain with the mother for five to nine months (grow to 300 to 700 pounds), then are grown for three to nine months, then are transported to a feedlot for finishing and are at the feedlot for 90 to 160 days, then are transported to slaughter.

As indicated above, in the second method herein, seaweed supplement is directly fed to the cattle during the feedlot finishing phase of the life cycle for beef production (the feedlot finishing period).

The cattle are the same as those described in conjunction with the first method herein.

The seaweed supplement for the second method herein is the same as that described generally and in detail in conjunction with the first method herein, and preferably is seaweed extract from *Ascophyllum nodosum* as described in conjunction with the first method herein.

The seaweed supplement is fed, for example, in an amount ranging from 0.5 to 1.5% by weight of the diet for at least 10 days during the feedlot finishing period, and preferably for at least 10 days (e.g., 10–20 or 14–20 days) at the beginning or at the end of the feedlot finishing period. The diet referred to can be any of those normally associated with feedlot finishing and is most typically based on corn but may be based instead on wheat, barley or other grains and includes the diets for feedlot finishing set forth in Examples I and II hereinafter. Periods of feeding 1% seaweed extract from *Ascophyllum nodosum* by weight of the diet of 14 days at the beginning and 14 days at the end of the feedlot finishing period were used, and in the two periods the better results were obtained using the 14 day period at the end of the feedlot finishing period (i.e., directly before slaughter). Color as indicated by estimated oxymyoglobin content was in the desirable range, i.e., over 18, for at least 8 days postmortem, almost until day 9 postmortem, compared to about 6 days postmortem where seaweed supplement was not fed, thereby showing extending of shelf-life at optimum prices for more than 1 day, i.e., about 2 days. In one alternative, the meat obtained by the second method herein is maintained on store shelves at optimum prices for a period longer than is the case without the treatment of the second method herein, e.g., up to 9 days.

We turn now to the third method herein wherein seaweed supplement is fed to swine during the nursery phase of the life cycle for pork production.

In a typical life cycle for pork production, piglets remain with the mother 14 to 28 days, then are removed from mother and put into a nursery for three to five weeks, then are moved to a finishing barn where they are kept until reaching 220 to 275 pounds (three to four months), then are transported to slaughter.

In the third method herein, the seaweed supplement is fed to the pigs after removal from the mother and before they are placed in a finishing barn, or in the life cycle described above when they are in the nursery.

The seaweed supplement for the third method herein is the same as that described generally and in detail in conjunction with the first method herein, and preferably is seaweed extract or seaweed meal from *Ascophyllum nodosum* as described in conjunction with the first method herein. The seaweed supplement is very preferably seaweed extract from *Ascophyllum nodosum*.

The seaweed supplement is fed, for example, at least 5 days or at least 10 days when the piglets are in the nursery, e.g., the first 10 to 15 days at the beginning of the period or the last 10 to 15 days at the end of the period when the piglets are in the nursery in an amount of 0.5 to 1.5% by weight of the diet, e.g., in an amount of 1% by weight of the diet. The diet referred to can be any of those normally fed to piglets in the nursery, e.g., 60–65% by weight milo (sorghum), 30–35% by weight soybean meal, and up to about 5% by weight vitamins and minerals and other additives, e.g., growth promotant.

Feeding said seaweed extract or seaweed meal in an amount of 1% by weight of diet for the first 10 days of the nursery period was found to increase the redness of meat color and feeding of said seaweed extract in an amount of 1% by weight of diet for the first 10 days of the nursery period was found to result in longer shelf-life where the meat was salable at optimum prices. In one alternative, the meat obtained in the third method herein is maintained on store shelves at optimum prices for a period longer than is the case without the treatment of the third method herein.

The methods of the invention herein are illustrated by the following working examples.

EXAMPLE I

In each of 1996 and 1997, 48 weaned steers were grazed in tall fescue pastures from April to October at Southwest Virginia Agricultural Research and Extension Center at Glade Spring (81° 40'west longitude; 30° 47'north latitude; 652 meters elevation) and 48 weaned steers were grazed in tall fescue pastures at Prairie Research Unit, Prairie, Miss. (88° 40' west longitude; 33° 50' north latitude; 984 meters elevation). Thus 192 steers were involved in the experiment. At each location, there were eight pastures, four that were established with endophyte (*Neotyphodium coenaphialum*) infected 'Kentucky-31' (KY-31) tall fescue and four that were established with KY-31 tall fescue that was not endophyte infected.

Two of each four endophyte-infected pastures at each location and two of each four pastures that were not endophyte infected at each location were sprayed with a water solution of seaweed extract. The seaweed extract was Acadian Soluble Seaweed Extract Powder and was commercially available and obtained from Acadian Seaplants Ltd., Dartmouth, Nova Scotia, Canada. The seaweed extract was obtained from *Ascophyllum nodosum* seaweed by alkaline hydrolysis extraction. The seaweed extract was dissolved for application in amount of 3 lbs seaweed extract per 30 gallons of water and was applied in the amount of 3 lbs per acre (3.4 kg/ha) in April and again about mid-summer. The spraying was carried out with a commercial field-type of sprayer.

The pastures that were endophyte infected that were sprayed with seaweed extract are designated E+S+. The pastures that were endophyte infected that were not sprayed with seaweed extract are designated E+S−. The pastures that were not endophyte infected that were sprayed with seaweed extract are designated E−S+. The pastures that were not endophyte infected that were not sprayed with seaweed extract are designated E−S−.

The steers pastured in Virginia were Angus and Angus× Hereford steers (initial body weight 265 kg; standard deviation equal to 5 kg). The steers pastured in Mississippi were ¼ Brahman×¾ Angus steers (initial body weight 250 kg; standard deviation equal to 2 kg).

Each pasture was 1.5 ha and six steers were grazed on each pasture, so the stocking rate was one steer per 0.25 ha.

At the end of the grazing season in October in each year, steers from both locations were transported by truck to the Burnett Center of Texas Tech University for finishing on the feedlot (101° 47' west longitude; 33° 45' north latitude; 993 meters elevation). Thus, in each year there were 48 steers from Virginia and 48 steers from Mississippi for a total of 96 steers in each year.

Steers were allotted to pens in the feedlot in a randomized block design with steers from both locations and each of the four pasture treatment within each block. Steers grouped together on pasture remained as a group on the feedlot so there were 6 steers per pen. All steers were fed the same diets based on steam flaked milo (*Sorghum bicolor*) and cottonseed hulls (*Gossipium hirsutum*). A first receiving diet (Receiving 1) was fed for two weeks followed by a second receiving diet (Receiving 2) being fed for two weeks, followed by an intermediate diet for two weeks, followed by a finishing diet. The diets are set forth in Table 1 below where AS-700 is Aureo S 700 (a chlortetracycline plus sulfamethazine) which is a growth promotant for cattle, where Rumensin premix is an efficiency additive and where Tylosin premix is a growth promotant.

TABLE 1

| | Diet | | | |
|---|---|---|---|---|
| Item | Receiving 1 | Receiving 2 | Intermediate | Finishing |
| | Percentage of Diet | | | |
| Steamflaked milo | 39.24 | 55.00 | 64.03 | 78.25 |
| Cottonseed hulls | 43.00 | 28.98 | 20.92 | 8.00 |
| Molasses, cane | 3.00 | 3.00 | 4.00 | 4.00 |
| Fat | 2.80 | 2.60 | 2.45 | 2.80 |
| Cottonseed meal | 2.80 | 2.50 | 2.50 | .00 |
| Corn gluten meal | 2.80 | 2.00 | 1.30 | 2.15 |
| Blood meal | 2.80 | 2.00 | 1.30 | .00 |
| Calcium carbonate | .94 | 1.06 | 1.15 | 1.27 |
| Dicalcium phosphate | .35 | .20 | .12 | .00 |
| Urea | .20 | .30 | .40 | .60 |
| Potassium chloride | .00 | .10 | .23 | .47 |
| Trace mineral premix | .23 | .24 | .25 | .26 |
| Sodium chloride | .15 | .15 | .15 | .14 |
| Vitamin A premix | .38 | .38 | .38 | .38 |
| Vitamin E premix | .09 | .09 | .09 | .09 |
| Rumensin premix | .37 | .55 | .73 | 1.00 |
| Tylosin premix | .00 | .00 | .00 | .60 |
| AS-700 | .85 | .85 | .00 | .00 |

Steers remained on the feedlot for 133 days in 1996 and for 160 days in 1997.

Steers were slaughtered in both 1996 and 1997, but evaluation for shelf-life was carried out only on meat from the steers slaughtered in 1997.

At slaughter in 1997, three steers within each of four pens were selected at random for evaluation of shelf-life of beef for each treatment (12 animals total for each of E+S+, E+S−, E−S+, and E−S−). At slaughter, primal cuts were obtained and the primal cuts were vacuum packaged using a Cryovar 8600 machine within 48 hours of slaughtering.

Meat was removed from vacuum packaging on day 7 after slaughter, day 14 after slaughter, day 21 after slaughter and day 28 after slaughter and, in each case, was evaluated on the first day after removal from vacuum packaging and daily thereafter. The evaluation period for the meat removed from vacuum packaging on day 7 is referred to as the period 1, for the meat removed from vacuum packaging on day 14 is referred to as the period 2, for the meat removed from vacuum packaging on day 21 is referred to as the period 3, and for the meat removed from vacuum packaging on day 28 is referred to as period 4.

Evaluation for shelf life was carried out for CEE Hunter L* values, CIE Hunter a* values, CIE Hunter b* values, by visual determination of color by a trained by panel, for discoloration (formation of green cast), for color uniformity and for browning (formation of brown cast).

CIE Hunter L* values were determined using a Minolta CR-200b machine (Japan) as described in "Guidelines for meat color evaluation" in Proceedings of the 44th Reciprocal Meat Conference, National Live Stock and Meat Board, Chicago, Ill., 1991, hereinafter AMSA, 1991 (where AMSA stands for American Meat Science Association). The determination was on a scale of 0–100 of lightness with 100 representing black.

CIE Hunter a* values were determined using a Minolta CR-200b machine (Japan) as described in AMSA, 1991. The determination was for redness with higher values representing cherry red and with lower values representing deviation from cherry red.

CIE Hunter b* values were determined using a Minolta CR-200b machine Japan as described in AMSA, 1991. Higher values represent yellow and lower values represent blue.

Visual color determinations were carried out by a trained panel of experts with above 5 representing the bright cherry red color associated with good color of meat, 4 to 5 representing darkening of red color to where the meat is salable but not at optimum prices and below 4 representing darkening to the point where the meat is unsalable as pieces of meat and must be used for hamburger. In particular, the scale is as follows: 8 represents extremely bright cherry red; 7 represents bright cherry red; 6 represents moderately bright cherry red; 5 represents slightly bright cherry red; 4 represents slightly dark cherry red; 3 represents moderately dark red; 2 represents dark red; and 1 represents extremely dark red.

Surface discoloration was determined as described in AMSA, 1991 with 1 being perfect (no discoloration), and values above 2 representing discoloration (green cast) to the point where the meat is not salable. In particular, the scale is as follows: 1 represents none of surface being discolored; 2 represents 1–19% of surface being discolored; 3 represents 20–39% of surface being discolored; 4 represents 40–59% of surface being discolored; 5 represents 60–79% of surface being discolored; 6 represents 80–99% of surface being discolored; and 7 represents 100% of surface being discolored.

Color uniformity was determined as described in AMSA, 1991. Determination was made for two-toning, i.e., the presence of more than one color shade, with 1 being perfect (no two-toning) and values above 2 representing two-toning to the extent that the meat was not salable. In particular, the scale is as follows: 1 represents uniformity; 2 represents slightly two-toned; 3 represents small amount of two-toning; 4 represents moderate amount of two-toning; and 5 represents extreme two-toning.

Browning was determined as described in AMSA, 1991. Determination was made using a six point scale with 1 representing no browning and 2½ representing browning to the point where the meat cannot be sold. In particular, the scale is as follows: 1 represents no browning; 2 represents dulling; 3 represents a grayish color; 4 represents a brownish-gray color; 5 represents a brown color; and 6 represents a dark brown color.

The results are set forth below.

CIE Hunter L* values determined are shown in FIG. 1. The data shows that removal from vacuum packaging resulted in darkening (P<0.01) over time within the first, second and last periods but no change in lightness or darkness of the meat occurred in period 3 (days 21 to 24). See FIG. 1. No effects of treatment on darkness were observed except during period 4 where meat from steers that grazed endophyte infected tall fescue was slightly lighter (P<0.05) than meat from steers that grazed tall fescue that was not endophyte infected. Values in FIG. 1 are mean values with n=4 pens (12 animals). In FIG. 1 "a" indicates statistical significance because of the day of removal from vacuum packaging (P<0.01) and "b" indicates statistical significance of effect of endophyte (P<0.05).

Figure 2:
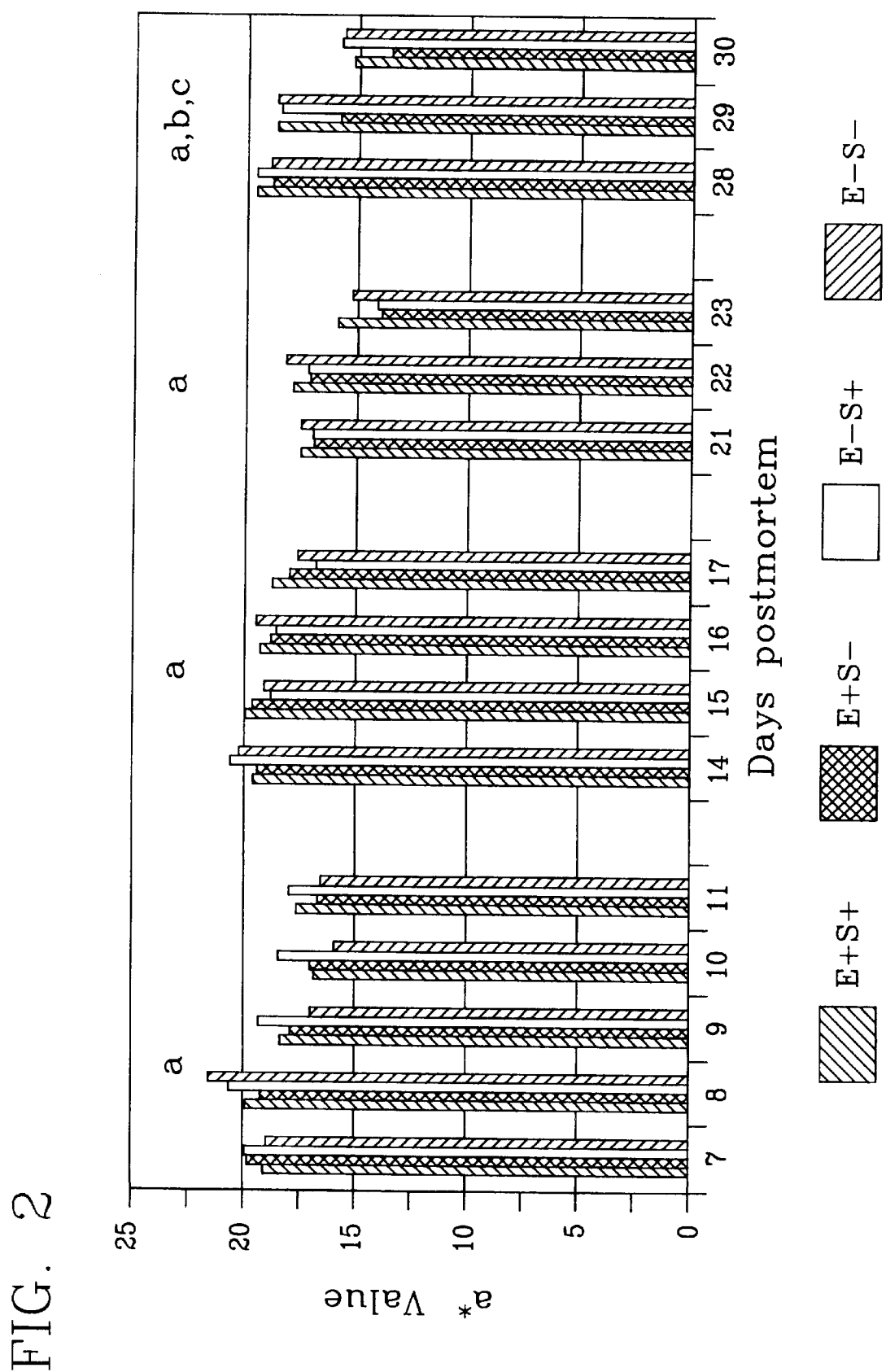
FIG. 2 depicts bar graphs showing CIE Hunter $a^*$ values for beef as described for FIG. 1.

CIE Hunter a* values determined are shown in FIG. 2. The data shows that redness of meat declined (P<0.01) over time after removal from vacuum packaging during each of the four periods. During days 28 to 30 (FIG. 2), meat from steers that had grazed seaweed extract treated pastures maintained a more desirable red color (P<0.10) than meat from steers that had grazed the non-seaweed treated fescue. On day 29, meat from steers that had grazed endophyte infected fescue had a more desirable red color (P<0.01) if the pasture had been treated with seaweed extract than if the pasture had not been treated with seaweed extract. The difference tended to be present on day 30 as well (P<0.16). Exposure to the endophyte in tall fescue resulted in a less desirable red color of meat (P<0.13) than in meat from steers grazing on fescue that was not endophyte infected. Values in FIG. 2 are mean values with n=4 pens (12 animals). In FIG. 2, "a" indicates statistical significance because of day of removal from vacuum packaging (P<0.01), "b" indicates statistical significance of seaweed extract treatment (P<0.10), and "c" indicates statistical significance of effect of endophyte infection (P<0.13).

Figure 3:
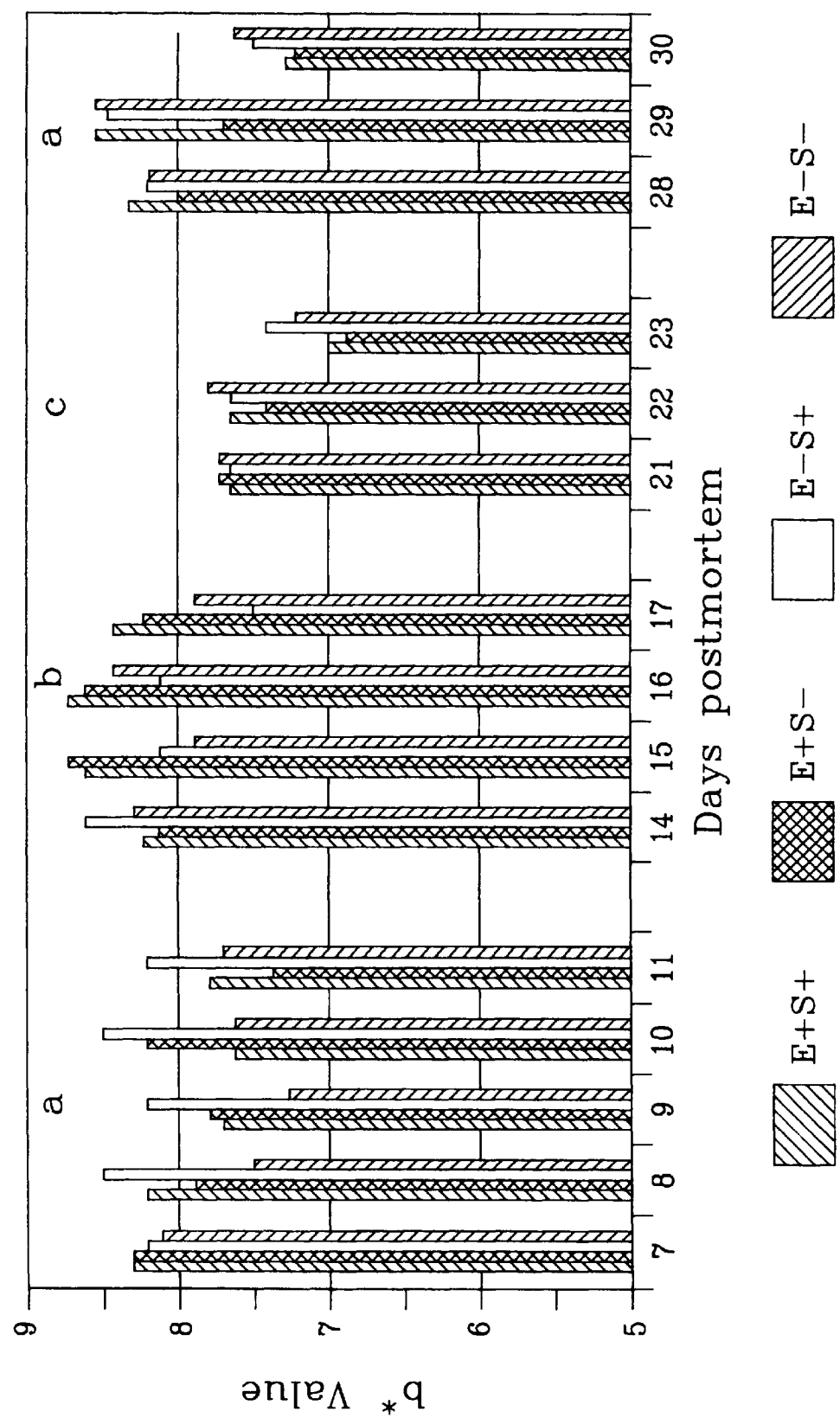
FIG. 3 depicts bar graphs showing CIE Hunter $b^*$ values for beef as described for FIG. 1.

CIE Hunter b* values determined are shown in FIG. 3. The data shows that the degree of yellowness or blueness of the meat as measured by CEE Hunter b* values was influenced by length of time after removal from vacuum packaging with values decreasing over time. However, over the fourth day in period 2, the decline was only observed in meat from steers grazed on fescue that was not endophyte infected. Values in FIG. 3 are mean values with n=4 pens (12 animals). In FIG. 3, "a" indicates statistical significance of length of time after removal from vacuum packaging (P<0.06), "b" indicates a day after removal from vacuum packaging×presence of endophyte infection interaction (P<0.05), and "c" indicates statistical significance of day of removal from vacuum packaging (P<0.05).

Figure 4:
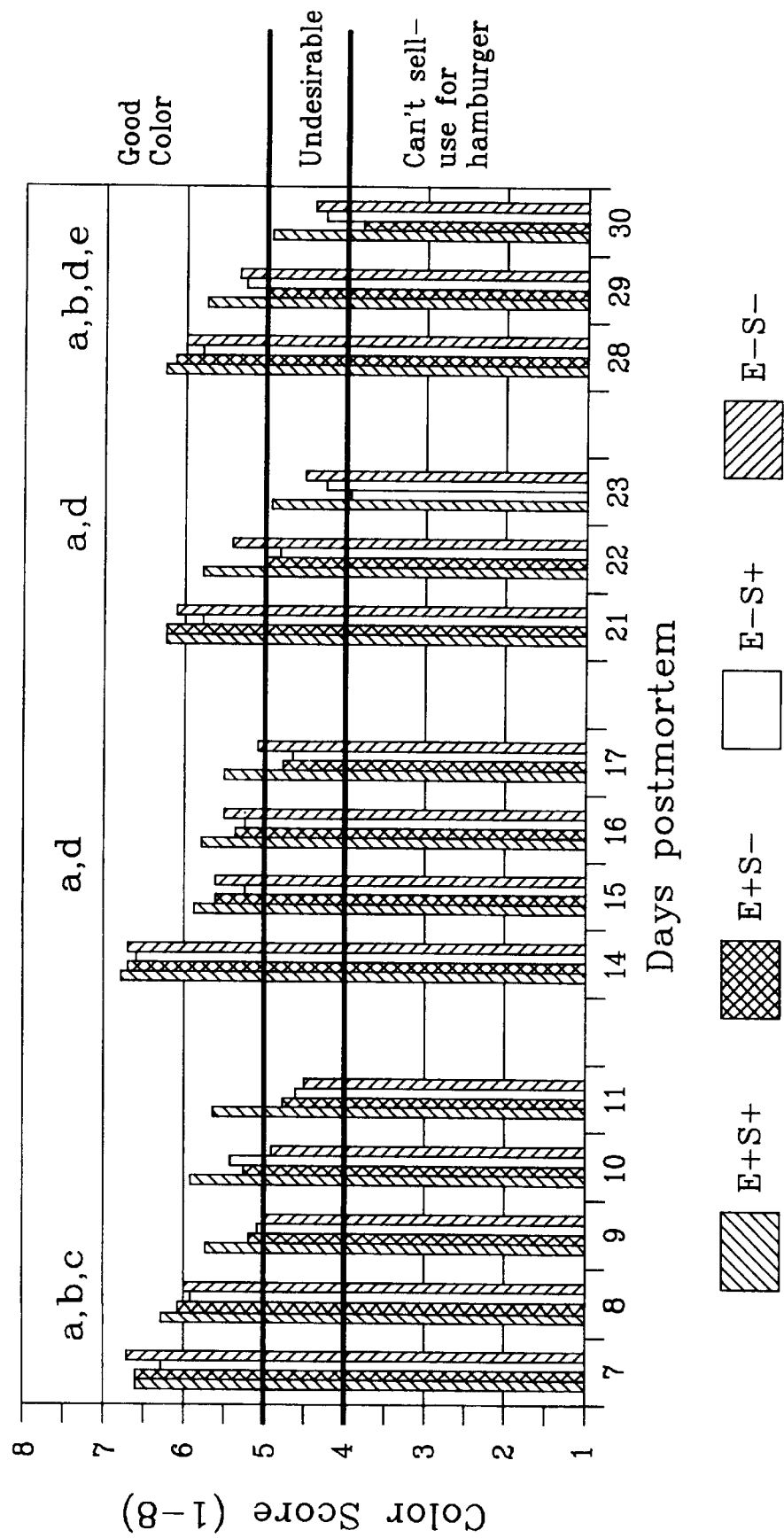
FIG. 4 depicts bar graphs showing visual color values for beef as described for FIG. 1.

Visual color determinations are shown in FIG. 4. The data indicates that meat from steers that had grazed endophyte infected tall fescue treated with seaweed extract maintained a more desirable red color (P<0.12) and was the only meat that remained desirable for sale after the second day in periods 3 and 4 (FIG. 4). Color declined (P<0.01) over time in all periods. In period 1, there was less color change in the color of meat from steers that had grazed fescue that was seaweed treated than fescue that was not seaweed treated (seaweed×day after removal from vacuum packaging interaction, P<0.05). Meat from steers that had grazed endophyte infected tall fescue maintained a more desirable red color during period 1 than steers that had grazed tall fescue that was not infected but this effect was not observed during the other three periods. During periods 2, 3 and 4, color declined more in meat from steers grazing on endophyte infected fescue that was not seaweed extract treated than in meat from steers grazing endophyte infected fescue that was seaweed extract treated but the effect of seaweed extract treatment was reversed for fescue that was not endophyte infected (endophyte infection×seaweed treatment×day of removal from vacuum packaging interaction; P<0.05). During the final period (days 28 to 30), meat from steers had a more desirable red color if steers had grazed seaweed extract treated pastures (P<0.08) but the effect was due to the large difference (P<0.001) in meat between cattle grazed on seaweed extract treated and untreated endophyte infected fescue by day 30. Values in FIG. 4 are mean values for n=4 pens (12 animals). In FIG.

4, "a" indicates significance of effect of length of time after removal from vacuum packaging (P<0.01), "b" indicates a seaweed extract treatment×day after removal from vacuum packaging interaction (P<0.01), "c" indicates significant effect of endophyte infection (P<0.12), "d" indicates a seaweed extract treatment by endophyte×day after removal from vacuum packaging interaction (P<0.05), and "e" indicates a significant effect of treatment with seaweed extract (P<0.08).

Figure 5:
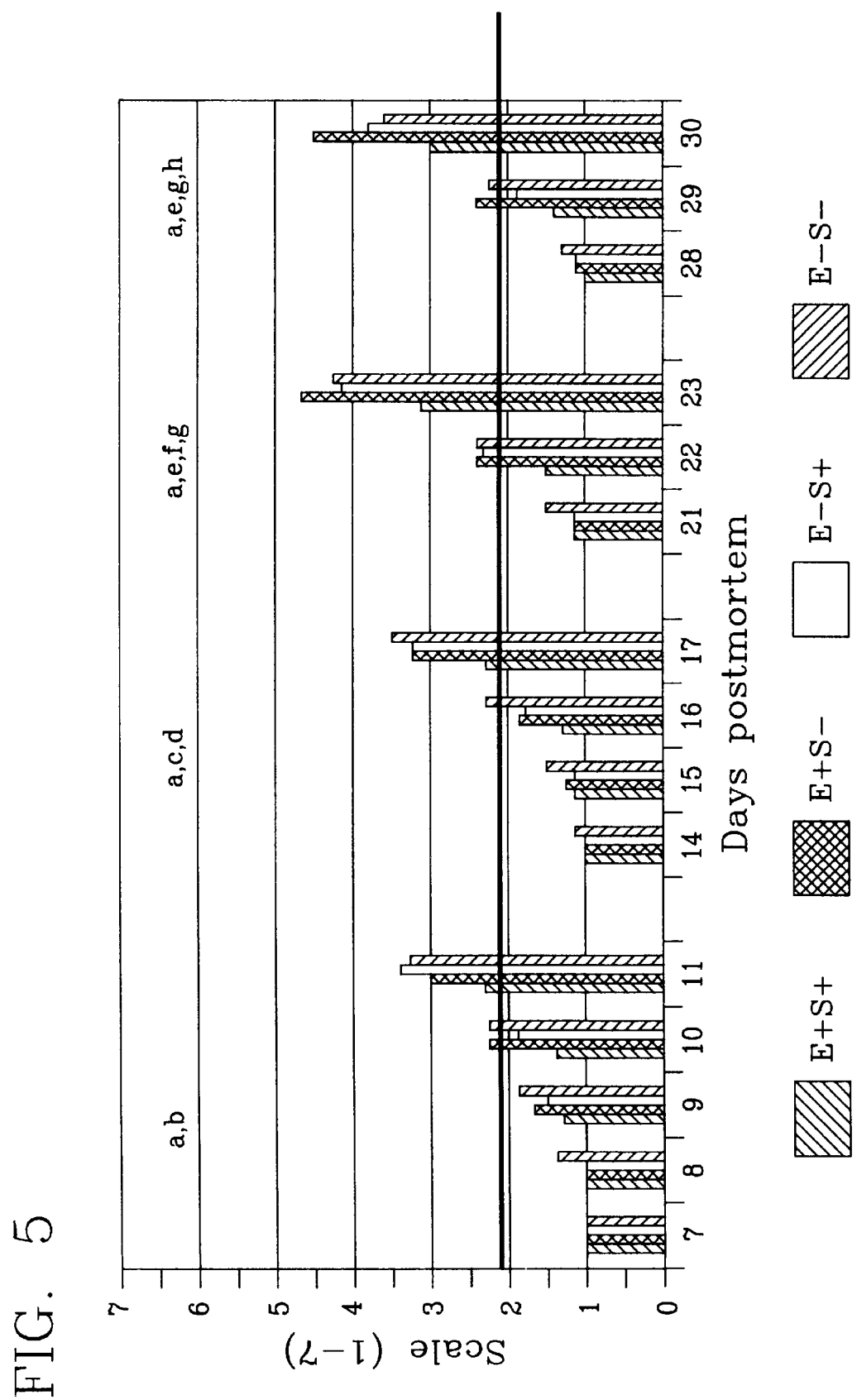
FIG. 5 depicts bar graphs showing surface discoloration values for beef as described for FIG. 1.

FIG. 5 shows values for surface discoloration determinations. The data shows discoloration of meat increased during each period. During period 1, surface discoloration deteriorated to a greater extent in meat from steers that had grazed in Mississippi on fescue that was not endophyte infected than in meat from steers grazing otherwise (location× endophyte infection×day after removal from vacuum packaging interaction; P<0.01). Seaweed extract treatment of pastures resulted in less surface discoloration during periods 2 (P<0.08), 3 (P<0.05), and 4 (P<0.05) than when seaweed extract was not applied. During periods 3 and 4, grazing on endophyte infected tall fescue which was not seaweed extract treated resulted in greater surface discoloration by day 3 after removal from vacuum packaging than when steers grazed fescue not infected by endophyte but application of seaweed extract to endophyte infected fescue reversed this effect (seaweed extract treatment×endophyte infection×day after removal from vacuum packaging interaction; P<0.05). During period 4, seaweed extract application reduced discoloration more in meat from steers from Mississippi than in meat from steers from Virginia (seaweed×location interaction; P<0.05). Each value is the mean of results from four pens (12 animals). In FIG. 5, "a" indicates significant effect of day after removal from vacuum packaging (P<0.01), "b" indicates significant effect of location×endophyte infection×day after removal from vacuum packaging interaction (P<0.01), "c" indicates significant effect of seaweed extract application (P<0.08), "d" indicates significant effect of endophyte infection (P<0.12); "e" indicates significant effect of seaweed extract application (P<0.05), "f" indicates significant effect of endophyte infection (P<0.10), "g" indicates a seaweed extract× endophyte infection×day after removal from vacuum packaging interaction (P<0.05), and "h" indicates a seaweed extract application×location interaction (P<0.05).

Figure 6:
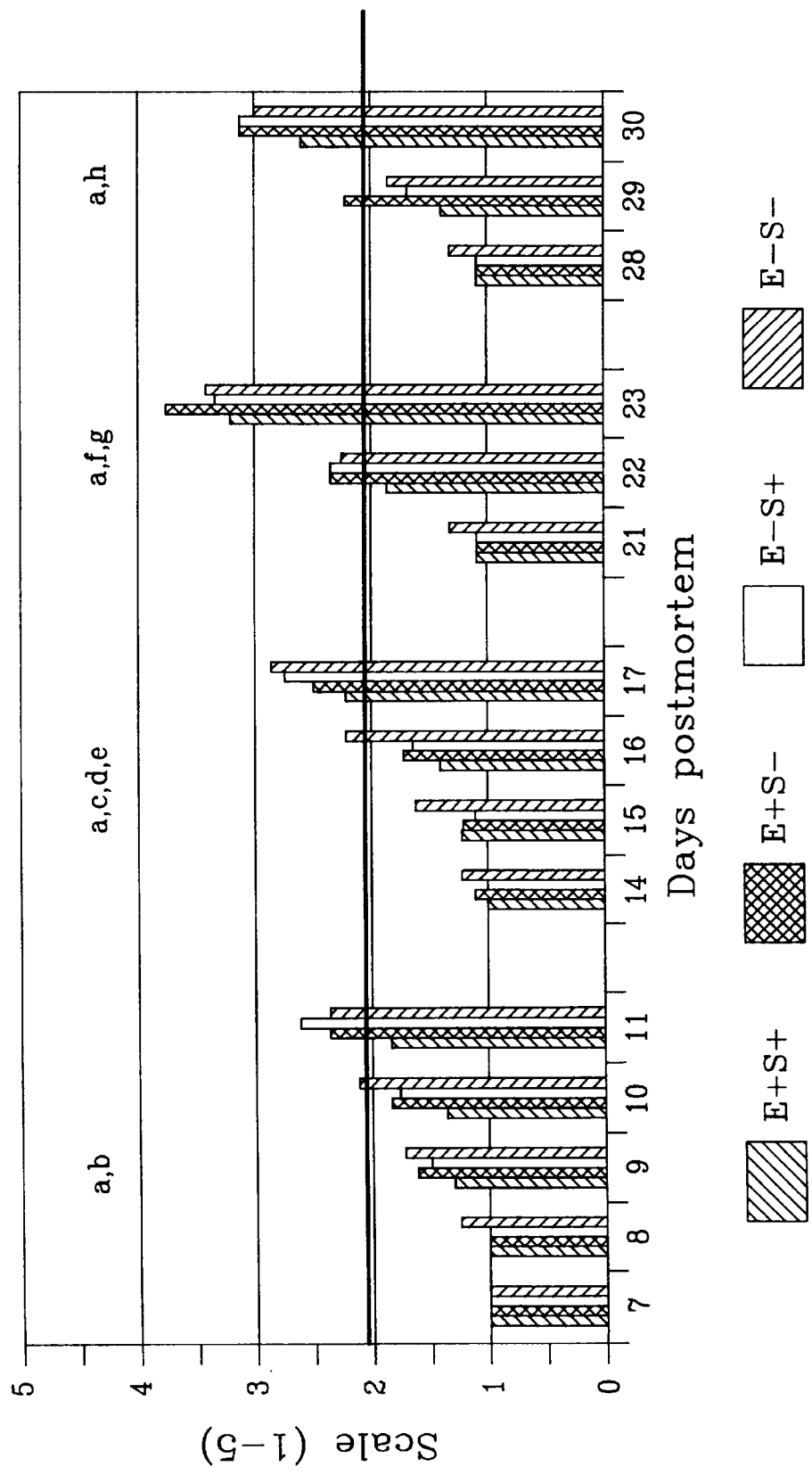
FIG. 6 depicts bar graphs showing color uniformity values for beef as described for FIG. 1.

Color uniformity determinations are shown in FIG. 6. The data shows that color uniformity deteriorated (P<0.01) over time within each of the four periods. By the fifth day after removal from vacuum packaging in period 1, all meat other than that from steers grazed on seaweed extract treated endophyte infected fescue had sufficient two-toning that the meat would have been removed from sale. In periods 2 (P<0.06), 3 (P<0.08), and 4 (P<0.05) meat from steers grazed on seaweed extract treated fescue had less two-toning than meat from steers grazed on fescue that was not seaweed extract treated. In periods 2 and 4, the effects of seaweed extract treatment were consistent across endophyte infection or non-infection and day after removal from vacuum packaging. On day 23 of the third period, the effects of seaweed extract treatment across endophyte infection or non-infection were also present, but on days 21 and 22, effects of seaweed extract treatment were less consistent (endophyte infection×seaweed extract treatment×day after removal from vacuum packaging; P<0.05). Values in FIG. 6 are mean values with n=4 pens (12 animals). In FIG. 6, "a" indicates significant effect of day after removal from vacuum packaging (P<0.01), "b" indicates significant effect of endophyte infection (P<0.16), "c" indicates significant effect of seaweed extract treatment (P<0.06), "d" indicates significant effect of endophyte infection (P<0.06), "e" indicates endophyte infection×location interaction (P<0.05), "f" indicates a seaweed extract treatment×endophyte infection×day after removal from vacuum packaging interaction (P<0.05), "g" indicates significant effect of seaweed extract treatment (P<0.08), and "h" indicates significant effect of seaweed extract treatment (P<0.05).

Figure 7:
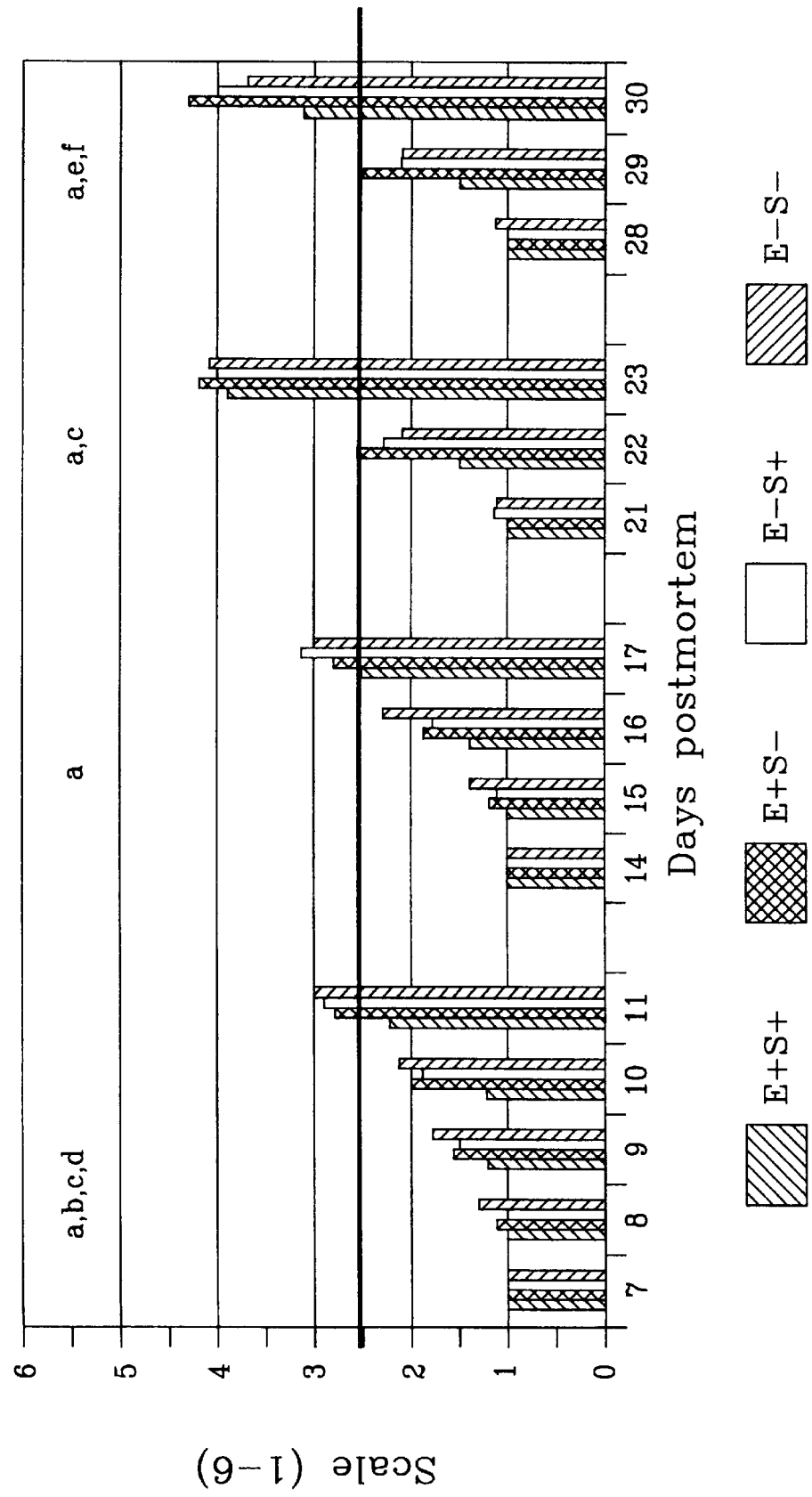
FIG. 7 depicts bar graphs showing browning grades for beef as described for FIG. 1.

Browning determinations are shown in FIG. 7. The data shows that browning of meat increased (P<0.01) over days after removal from vacuum packaging during each of the four periods. In period 1, meat from steers that grazed on fescue that was not endophyte infected in Mississippi exhibited a more rapid rate of browning than in other cases (location×endophyte infection×day after removal from vacuum packaging interaction; P<0.05). Degree of browning of the meat was higher for steers grazed on fescue not infected with endophyte than for meat from steers grazed on endophyte infected fescue (P<0.17) and was decreased (P<0.15) if the pasture was treated with seaweed extract. During period 3, seaweed extract treatment of endophyte infected fescue resulted in meat with much less browning than in meat from steers grazed on endophyte infected fescue that was not seaweed extract treated but the effect of seaweed extract treatment was inconsistent for fescue that was not endophyte infected (seaweed×endophyte infection× days after removal from vacuum packaging interaction; P<0.05). During period 4, seaweed extract treatment of fescue caused reduction (P<0.05) in browning of meat of steers grazed thereon; this was due primarily to the large effect on meat from steers grazed on seaweed extract treated endophyte infected fescue. Values in FIG. 7 are mean values with n=4 pens (12 animals). In FIG. 7, "a" indicates significant effect of day after removal from vacuum packaging (P<0.01), "b" indicates a location×endophyte infection×day after removal from vacuum packaging interaction (<0.05), "c" indicates significant effect of endophyte infection (P<0.17), "d" indicates significant effect of seaweed extract treatment (P<0.15), "e" indicates a seaweed extract treatment×endophyte infection×day after removal from vacuum packaging interaction (P<0.05), and "f" indicates significant effect of seaweed extract treatment (P<0.05).

The data shows that for cattle grazed on seaweed extract treated fescue (endophyte infected and not endophyte infected) where primal cuts are removed from vacuum packaging seven days after slaughter, meat from the primal cuts remains desirable for sale on the fourth day after removal of the primal cuts from vacuum packaging while this is not the case for meat from primal cuts from cattle grazed on fescue (endophyte infected and not endophyte infected) that was not seaweed extract treated.

The data shows that for cattle grazed on seaweed extract treated fescue (endophyte infected and not endophyte infected), where primal cuts are removed from vacuum packaging 28 days after slaughter, meat from the primal cuts remains desirable for sale on the second day after removal of the primal cuts from vacuum packaging while this is not the case for meat from primal cuts from cattle grazed on fescue (endophyte infected and not endophyte infected) that was not seaweed extract treated.

The data shows that for cattle grazed on seaweed extract treated fescue (endophyte infected), where primal cuts are removal from vacuum packaging 21 days after slaughter, meat from the primal cuts remains desirable for sale on the second day after removal of the primal cuts from vacuum packaging while this is not the case for meat from primal cuts from cattle grazed on fescue (endophyte infected) that was not seaweed extract treated.

The data shows that for cattle grazed on seaweed extract treated fescue (not endophyte infected), where primal cuts are removed from vacuum packaging 14 days after slaughter, meat from the primal cuts remains desirable for sale on the third day after removal of the primal cuts from vacuum packaging while this is not the case for meat from primal cuts from cattle grazed on fescue (not endophyte infected) that was not seaweed extract treated.

Figure 8:
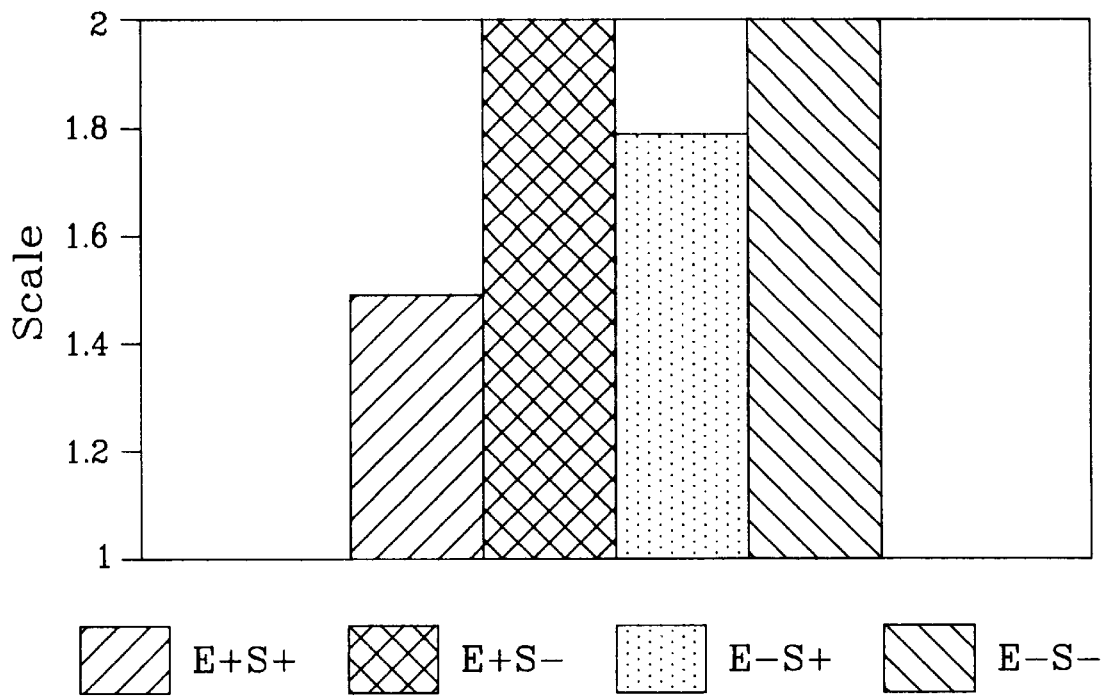
FIG. 8 depicts bar graphs showing overall summary data for all periods and all intervals for surface discoloration data on beef from steers that had grazed endophyte-infected (E+) and non-infected (E−1) fescue that was either treated (S+) or untreated (S−) with seaweed extract as described in Example I.
Figure 9:
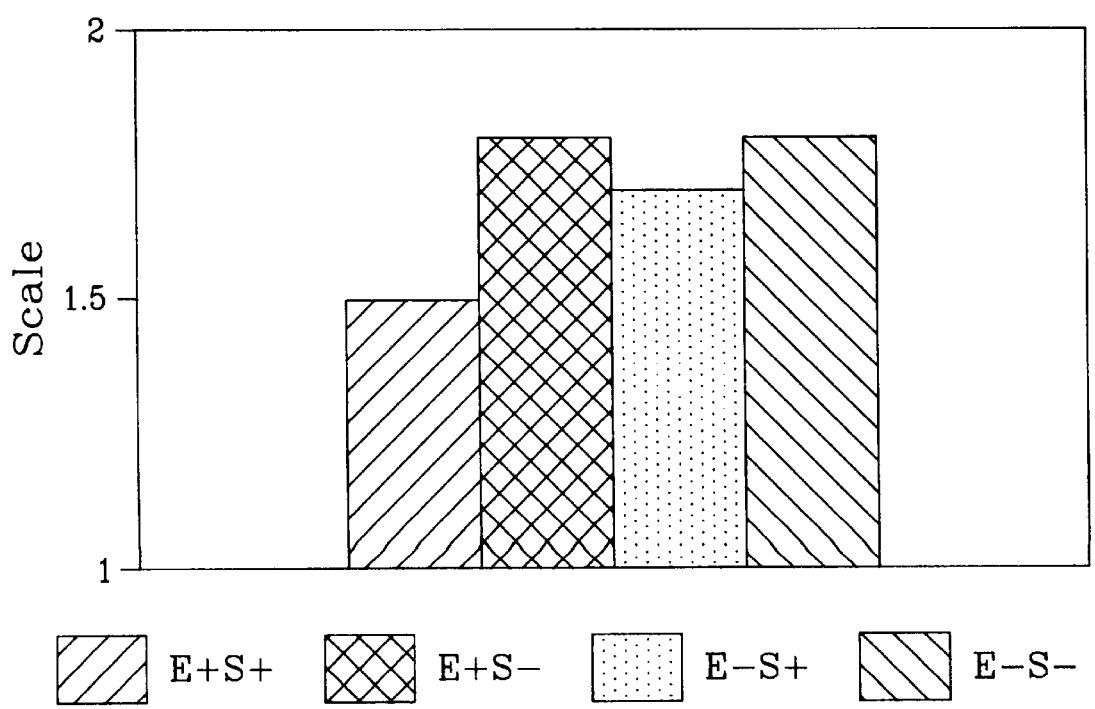
FIG. 9 depicts bar graphs showing overall summary data as for FIG. 8 but for color uniformity data.
Figure 10:
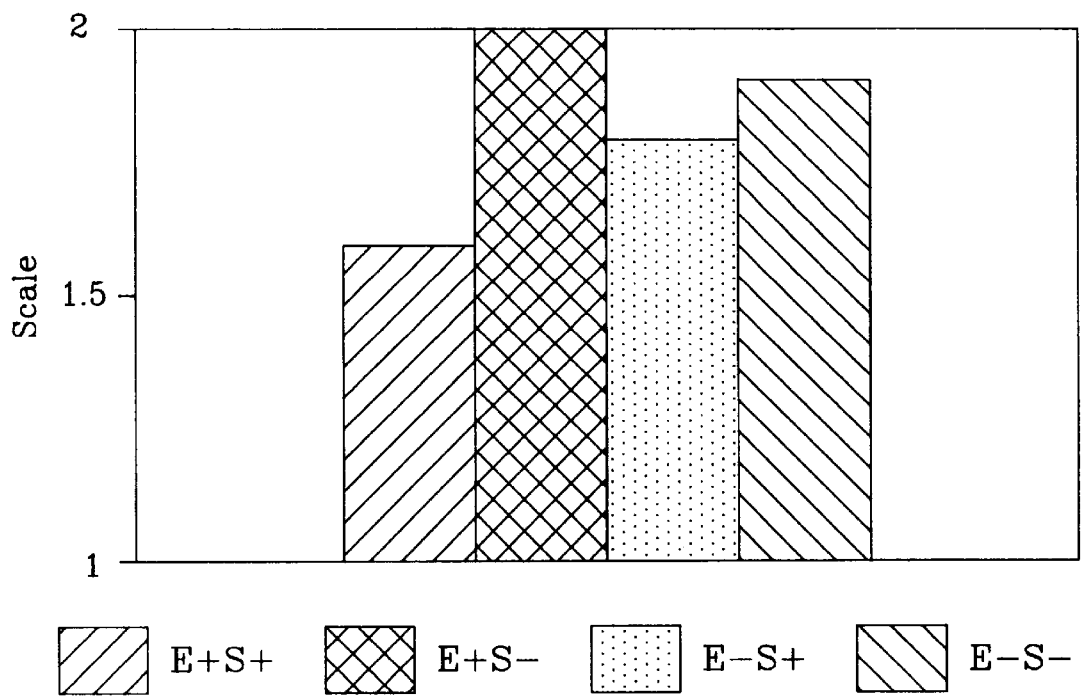
FIG. 10 depicts bar graphs showing overall summary data as for FIG. 8 but for browning data.
Figure 11:
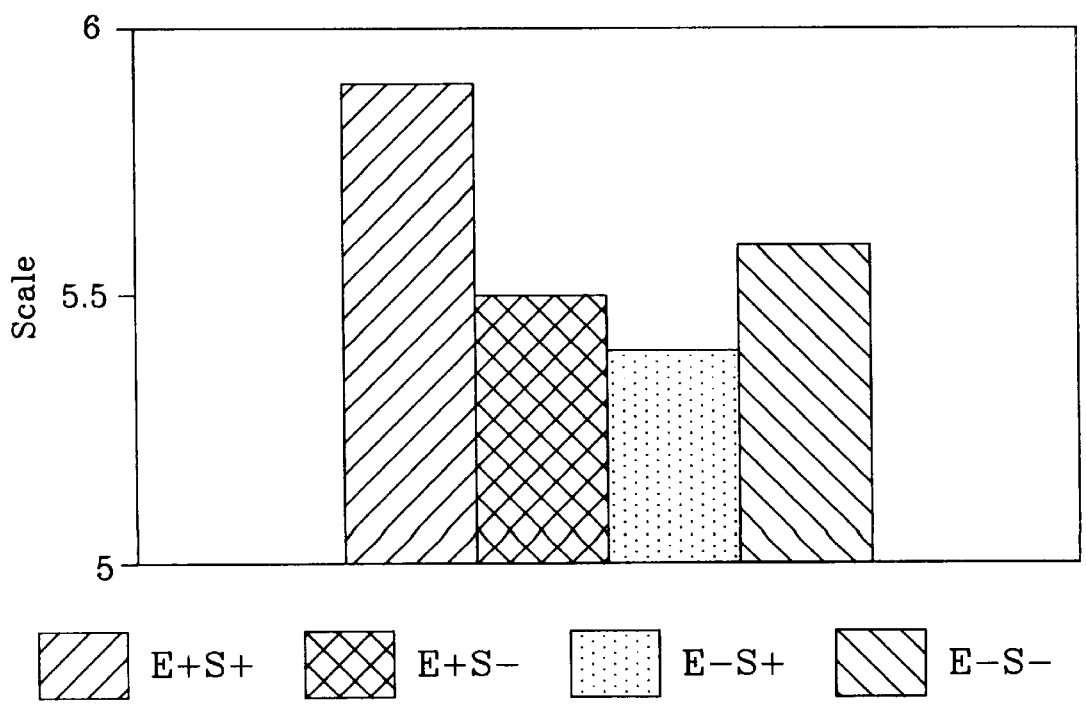
FIG. 11 depicts bar graphs showing overall summary data as for FIG. 8 but for visual color data.

Bar graphs were made up showing overall summary data for all periods and all intervals for the surface discoloration data (FIG. 8), for the color uniformity data (FIG. 9), for the browning data (FIG. 10), and for the visual color data (FIG. 11). As indicated in FIG. 8, the overall data for discoloration shows less discoloration (P<0.001) for seaweed extract treatment, less discoloration when the fescue is endophyte infected (P<0.01) and an endophyte infection×seaweed extract treatment interaction (P<0.01). As indicated in FIG. 9, the overall data for uniformity shows better uniformity results for seaweed extract treatment (P<0.0001). As indicated in FIG. 10, the overall data for browning indicates better results, i.e., less browning (P<0.001) for seaweed extract treatment, better results when the fescue is endophyte infected (P<0.01) and an endophyte infection×seaweed extract treatment interaction (P<0.01). As indicated in FIG. 11, the overall data for visual color shows better results for E+S+.

EXAMPLE II

Eighty-eight head of cattle were fed either a control diet or were fed seaweed extract (Acadian Soluble Seaweed Extract Powder) at 1% of diet for the first 14 days of the feedlot phase or for the last 14 days of the feedlot phase directly before slaughter.

Different diets were fed to five different groups of animals.

Diet 1 consisted by weight of 29.5% cottonseed hulls, 48.5% rolled corn, 13.25% soybean meal, 1.8% salt, 0.9% calcium, 0.24% milo (sorghum), 0.005% mineral oil, 0.005% Vitamin A, and 5.8% molasses.

Diets 2, 3, 4 and 5 consisted for silages and supplement. The silage for Diet 2 was the sorghum Brown Mid-rib. The silage for Diet 3 was the sorghum Fame. The silage for Diet 4 was the sorghum Cow Vittals. The silage for Diet 5 was corn silage. For the silage diets, for the growing phase of the feedlot phase (up until the last 60 days of the feedlot phase), the diets consisted by weight of 84.5% silage, 13% cottonseed meal, and 2.5% of supplement (vitamins, minerals, rumensin and tylosin), and for the finishing phase (last 60 days of the feedlot phase), the diets consisted by weight of 25% silage, 34.7% steam flaked corn, 13.8% cottonseed hulls, 9.4% alfalfa, 6.64% cottonseed meal, 5.2% molasses, 2.5% fat, 2.21 supplement (the same as for the growing phase), and 0.55% urea.

Evaluation of steaks was carried out for oxymyoglobin content, visual color scores, texture scores, CIE Hunter L* values, and hue angles.

Content of oxymyoglobin, the bright red pigment in meat that results in the characteristic and desirable red color of meats, was estimated using Minolta Colorimeter reflectance readings.

Visual color determinations were carried out as described in Example I.

Texture scores were determined by a trained panel of experts with increased scores indicating finer textures. An eight point scale was used with 8 being very fine texture (the most desirable).

CIE Hunter L* values were determined as described in Example I.

Hue angles were also determined. The hue angles were determined from Hunter a* and b* values with the result being compared to a color chart with the red zone of the color chart being good color.

The results are set forth below.

Figure 12:
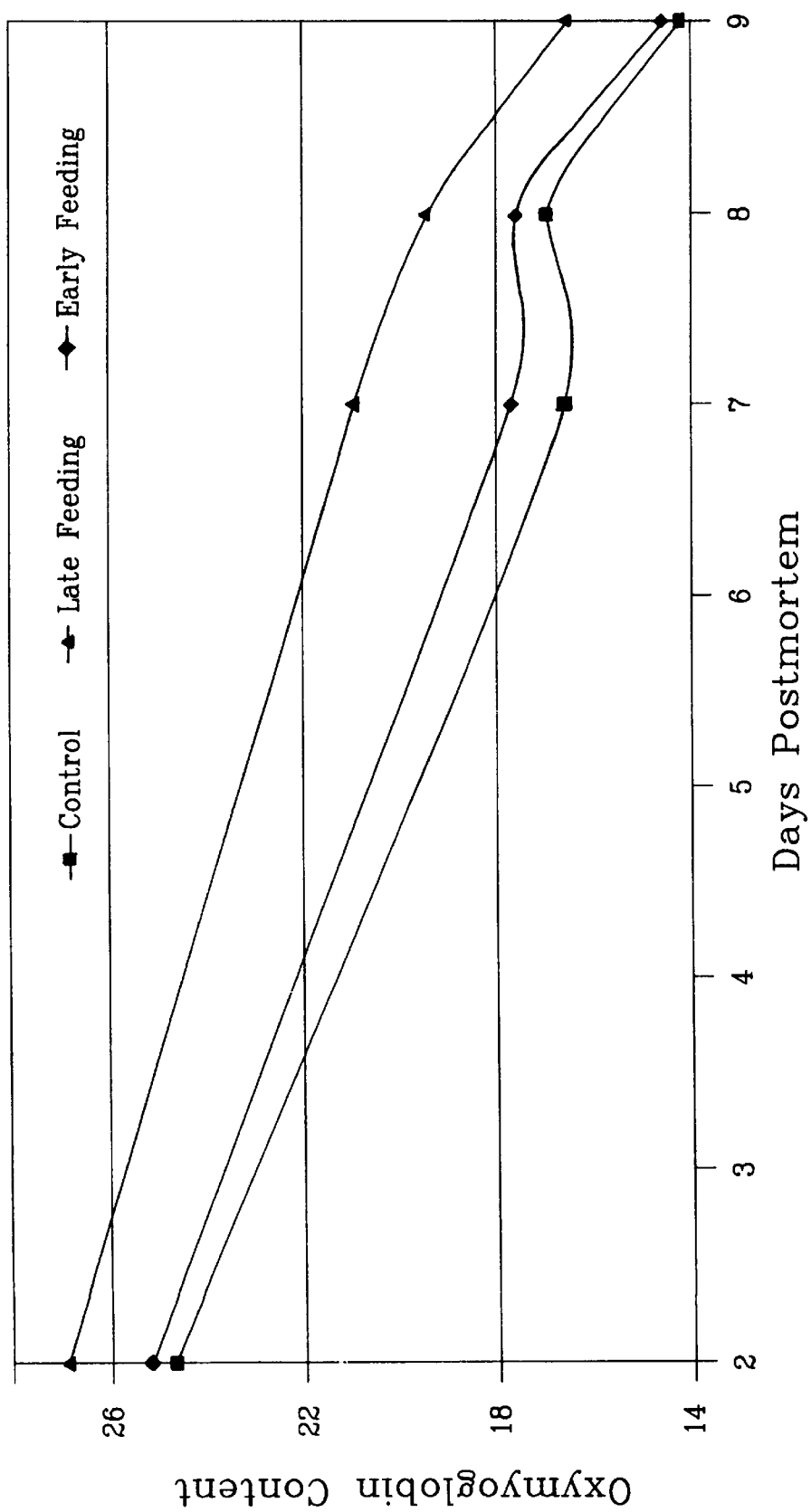
FIG. 12 depicts graphs showing measured color determination in terms of estimated oxymyoglobin content in beef steaks for experiments as described in Example II.

Oxymyoglobin contents determined for ribeye steaks are shown in FIG. 12 where the squares are values for control diets, the triangles are values for feeding seaweed extract the last 14 days of the feedlot phase (late fed animals or late feeding), and the diamonds are values for feeding seaweed extract the first 14 days of the feedlot phase (early fed animals or early feeding). Since there were no treatment by day interactions, values were averaged across days for statistical analysis. Oxymyoglobin contents of controls were undesirably low at 7 days postmortem while steaks from late fed animals remained in the desirable range until postmortem day 9. Results for steaks from early fed animals were consistently between those for steaks from the late fed animals, and for steaks from the control animals. The results for the late feeding showed increased oxymyoglobin content (P<0.01) compared with controls.

Figure 13:
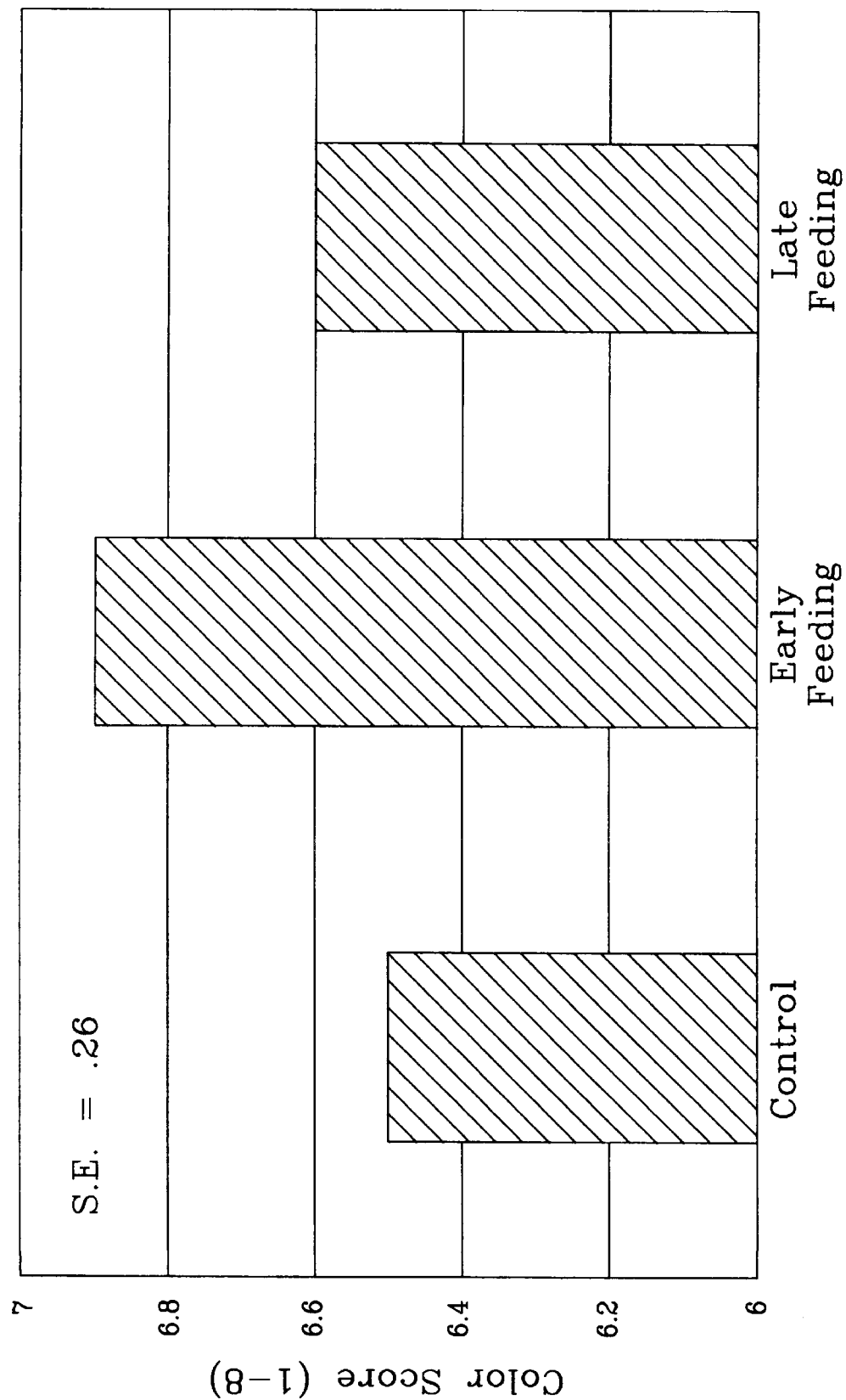
FIG. 13 depict bar graphs showing visual color values for ribeye steaks for experiments as described in Example II.

Results for visual color determinations for ribeye steaks are shown in FIG. 13. The steaks from steers fed the seaweed extract during the first 14 days of the finishing period (early feeding) had higher visual color scores (desirable) when compared with steaks from the controls (P<0.08). Steaks from steers fed seaweed extract during the last 14 days before slaughter (late feeding) also had more desirable color scores than steaks from control steers.

Results for texture determinations showed increased texture scores (P<0.02) for ribeye steaks from steers fed seaweed extract during the initial 14 days of the finishing period (moderately fine texture) when compared with ribeye steaks from control steers (slightly fine texture). Ribeye steaks from steers fed seaweed extract during the last 14 days of the finishing period also had higher texture scores than ribeye steaks from control steers.

Results of CEE Hunter L* values showed increased values for top loin steaks from steers fed seaweed extract the last 14 days of the finishing period when compared with top loin steaks from control steers (P<0.01) and were higher (P<0.07) than for top loin steaks from steers fed the extract during the first 14 days of the finishing period. Values obtained were in the 32–36 range; in this range, higher numbers indicated a color preferred by retail consumers.

Top loin steaks from steers fed seaweed extract the last 14 days of the finishing period resulted in higher hue angles when compared to top loin steaks from control steers (P<0.09) and compared to steaks from steers fed seaweed extract the first 14 days of the feeding period (P<0.03).

The seaweed treatments produced essentially the same results for all the diets.

EXAMPLE III

Sixty-four pigs were in the nursery phase of the life cycle for production (starting at 28 days old and lasting three to five weeks).

The 64 pigs were divided into groups of four, and four groups each were fed either seaweed meal (Acadian Kelp Meal) in amount of 1% by weight of diet for the first 10 days of the nursery phase, seaweed extract (Acadian Soluble Seaweed Extract Powder) in amount of 1% by weight of diet for the first 10 days of the nursery phase, seaweed meal (Acadian Kelp Meal) in amount of 1% by weight of diet for five weeks, or a control diet. The diet referred to consisted by weight of 64.275% ground milo (sorghum), 32.5% soybean meal, 0.3% salt, 1.4% dicalcium phosphate, 1.1% calcium and 0.425% vitamins, and this was supplemented by 1% by weight of the total of magnesium oxide and 0.85% by weight of the total of trace minerals.

Evaluation was carried out on pork chops for visual color scores and on pork muscle for oxymyoglobin content.

Visual color determinations were carried out as described in Example I.

Oxymyoglobin content was estimated using Minolta Colorimeter reflectance readings.

The results are set forth below.

Figure 14:
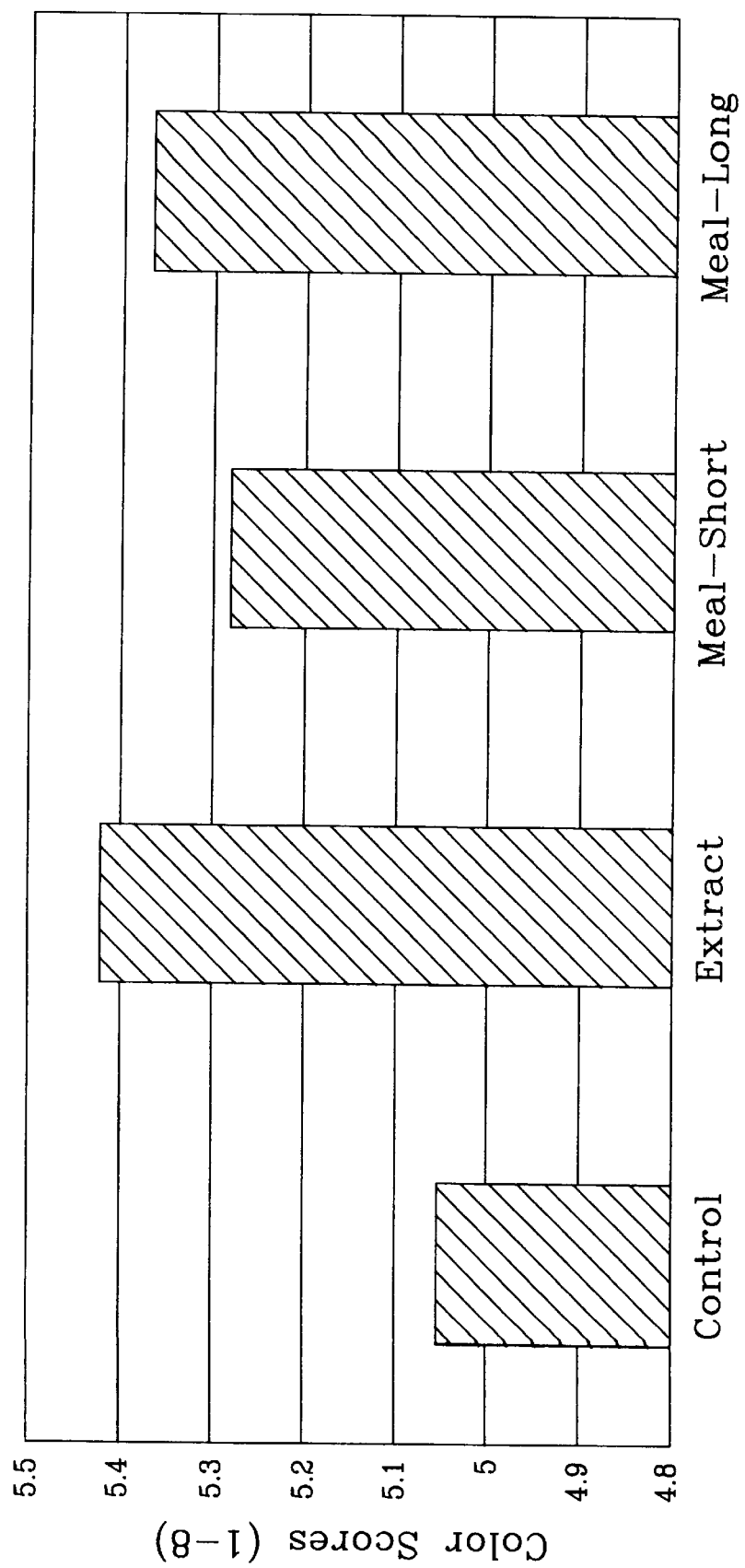
FIG. 14 depicts bar graphs showing visual color values for pork chops for experiments as described in Example III.

Results for visual color determinations for pork chops are shown in FIG. 14 where "Extract" denotes results for the pigs fed seaweed extract, "Meal-Short" denotes results for the pigs fed seaweed meal for 10 days and "Meal-Long" denotes results for pigs fed seaweed meal for five weeks. Direct feeding of seaweed, both extract and meal increased color scores compared with controls (P<0.05; S.E.=0.12) for pork chops during retail display conditions.

Figure 15:
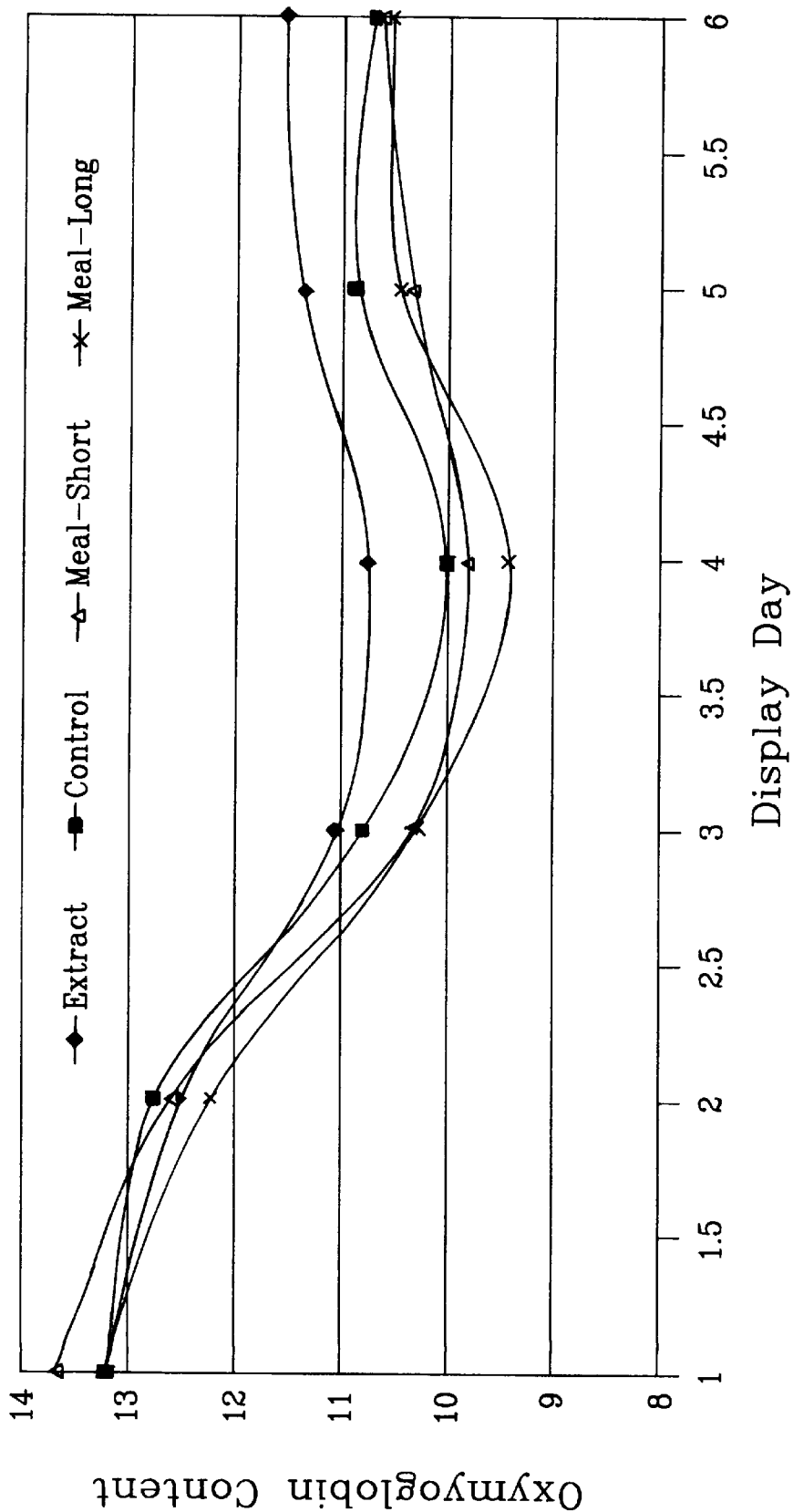
FIG. 15 depict graphs showing measured color determinations in terms of estimated oxymyoglobin content in pork muscle in experiments as described in Example III.

Results for oxymyoglobin contents are shown in FIG. 15 in which values are averaged across days and where the diamonds are values for feeding seaweed extract, the squares are values for control diets, the triangles are values for feeding seaweed meal for 10 days, and the X's are values for feeding seaweed meal for five weeks. Feeding of seaweed extract increased oxymyoglobin content (P<0.01) in pork muscle consistently in the display period compared with pork muscle from pigs fed seaweed meal during the five-week nursery phase.

Evaluations were also carried out on pork chops for color uniformity (determined as described in Example 1), lean discoloration and lean browning. Feeding seaweed extract had no effect on color uniformity, lean discoloration or lean browning over the display period compared with controls. Feeding seaweed meal during the entire five-week nursery phase decreased color uniformity (P<0.04) and increased lean discoloration (P<0.01) and lean browning (P<0.01) over display times compared with the control and to the 10 day feeding of seaweed meal.

Evaluations were also carried out on pork chops for CIE Hunter a* values (determined as described in Example I) and for chroma values (color saturation). Long-term (5-week) feeding of seaweed meal decreased (P<0.05) CIE Hunter a* values and chroma values compared to short-term (10-day) feeding of seaweed meal. The CIE Hunter a* values (P<0.01) and chroma values (P<0.06) were also higher for pigs fed the control diet than for pigs fed the long-term meal treatment.

Feeding seaweed extract for 10 days resulted in a more desirable color. Feeding seaweed meal for either 10 days or for the entire 5-week period resulted in a more desirable color but decreased other indicators of desirable shelf-life.

VARIATIONS

Variations of the above will be obvious to those skilled in the art. Thus, the scope of the invention is defined by the claims.

What is claimed is:

1. A method of obtaining beef of increased shelf-life comprising the steps of:
    (a) grazing cattle raised for meat production on forage on or into which seaweed supplement has been incorporated,
    (b) slaughtering the cattle and obtaining primal cuts of beef, thereby to obtain beef which has a surface discoloration value ranging from 1 to 2 for at least one day longer than if seaweed supplement was not incorporated.

2. The method of claim 1, wherein the forage is tall fescue grass.

3. The method of claim 1, wherein the seaweed supplement is incorporated by application of seaweed extract onto the forage.

4. The method of claim 3, wherein the seaweed extract is obtained by extraction of *Ascophyllum nodosum*.

5. The method of claim 4, wherein the forage is tall fescue grass.

6. The method of claim 5, wherein the primal cuts of beef are vacuum packaged within 36 to 48 hours after slaughtering.

7. The method of claim 6, wherein the primal cuts are removed from vacuum packaging seven days after slaughter, and meat from the primal cuts has a surface discoloration value of 2 or less for at least one day longer than if seaweed supplement was not incorporated.

8. The method of claim 6, wherein the primal cuts are removed from vacuum packaging 28 days after slaughter, and meat from the primal cuts has a surface discoloration value of 2 or less for at least one day longer than if seaweed supplement was not incorporated.

9. The method of claim 6, wherein the tall fescue grass is infected with an endophyte fungus.

10. The method of claim 9, wherein the endophyte fungus is *Neotyphodium coenophialum*.

11. The method of claim 10, wherein the primal cuts are removed from vacuum packaging 21 days after slaughter, and meat from the primal cuts has a surface discoloration value of 2 or less for at least one day longer than if seaweed supplement was not incorporated.

12. The method of claim 6, wherein the tall fescue grass is not infected with an endophyte fungus.

13. The method of claim 12, wherein the primal cuts are removed from vacuum packaging 14 days after slaughter, and meat from the primal cuts has a surface discoloration value of 2 or less for at least one day longer than if seaweed supplement was not incorporated.

14. The method of claim 1, wherein the meat from the primal cuts is maintained on the grocery store shelf for at least one day longer than meat from cattle grazed on forage on or into which seaweed supplement was not incorporated.

15. The method of claim 1 wherein the seaweed supplement is incorporated by the application of seaweed meal onto the forage.

16. The method of claim 1 where the cattle in step (a) are raised for production of meat for retail sale.

17. The method of claim 1 where the increased shelf-life is obtained irrespective of quality grade.

18. A method for obtaining beef of increased shelf-life comprising the steps of:
    (a) directly feeding seaweed supplement to cattle raised for meat production during the feedlot finishing period of the life cycle for beef production;
    (b) Slaugtering the cattle and obtaining primal cuts of beef;

thereby to obtain beef which has an oxymyoglobin content based on reflectance reading at least 2 to 3% higher than if seaweed supplement was not fed whereby the beef is salable in a grocery store at a higher price for at least one day longer than if seaweed supplement was not fed.

19. The method of claim 18, where the seaweed supplement is from *Ascophyllum nodosum*.

20. The method of claim 19, where the seaweed supplement is seaweed extract.

21. The method of claim 20, wherein the seaweed supplement is fed in an amount ranging from 0.5 to 1.5% by weight of the diet for at least 10 days during the feedlot finishing period.

22. The method of claim 21, where the seaweed supplement is fed for 10 to 20 days at the beginning or end of the feedlot finishing period.

23. The method of claim 22, where the seaweed supplement is fed for 10 to 20 days at the end of the feedlot finishing period.

24. The method of claim 23, where the beef obtained has an oxmyoglobin content based on a reflectance reading at least 2 to 3% higher than if seaweed supplement was not fed for at least 8 days postmortem.

25. The method of claim 24, where the beef obtained is maintained on store shelves for at least 8 days postmortem.

26. The method of claim 18 wherein the beef obtained has a higher visual color determination score than if seaweed supplement were not fed.

27. The method of claim 19 where the seaweed supplement is seaweed meal.

28. The method of claim 18 where the cattle in step (a) are raised for production of meat for retail sale.

29. The method of claim 18 where the increased shelf-life is obtained irrespective of quality grade.

30. A method of obtaining pork of increased shelf-life comprising the steps of:
   (a) feeding seaweed supplement to swine raised for pork production during the nursery period of the life cycle of swine raised for pork production;
   (b) slaughtering the swine;
thereby to obtain pork having a higher visual color determination score during retail display than if seaweed supplement were not fed.

31. The method of claim 30 where the seaweed supplement is seaweed extract obtained from *Ascophyllum nodosum* fed in amount of 0.5 to 1.5% by weight of the diet.

32. The method of claim 31 where the seaweed supplement is fed for the first 10 to 15 days of the nursery period.

33. The method of claim 31 where the seaweed extract is fed for the last 10 to 15 days of the nursery period.

34. The method of claim 31 wherein the pork obtained has muscle with increased oxymyoglobin content based on a reflectance reading than if seaweed supplement were not fed during retail display.

35. The method of claim 30 where the seaweed supplement is seaweed meal.

36. The method of claim 30 where the swine in step (a) are raised for production of pork for retail sale.

\* \* \* \* \*